(12) United States Patent
Navarro de Lara et al.

(10) Patent No.: US 12,390,122 B2
(45) Date of Patent: Aug. 19, 2025

(54) SYSTEM AND METHOD FOR INTEGRATED MAGNETIC RESONANCE IMAGING (MRI) AND ELECTROENCEPHALOGRAM (EEG)

(71) Applicant: The General Hospital Corporation, Boston, MA (US)

(72) Inventors: Lucia Isabel Navarro de Lara, Medford, MA (US); Aapo Nummenmaa, Boxford, MA (US)

(73) Assignee: The General Hospital Corporation, Boston, MA (US)

( * ) Notice: Subject to any disclaimer, the term of this patent is extended or adjusted under 35 U.S.C. 154(b) by 99 days.

(21) Appl. No.: 18/310,380

(22) Filed: May 1, 2023

(65) Prior Publication Data

US 2023/0346246 A1    Nov. 2, 2023

Related U.S. Application Data

(60) Provisional application No. 63/336,596, filed on Apr. 29, 2022.

(51) Int. Cl.
*A61B 5/00* (2006.01)
*A61B 5/055* (2006.01)
*A61B 5/291* (2021.01)
*A61N 2/00* (2006.01)

(52) U.S. Cl.
CPC .............. *A61B 5/055* (2013.01); *A61B 5/291* (2021.01); *A61B 5/6803* (2013.01); *A61N 2/006* (2013.01)

(58) Field of Classification Search
CPC .................................................... A61B 5/6803
See application file for complete search history.

(56) References Cited

U.S. PATENT DOCUMENTS

| 8,690,748 | B1 * | 4/2014 | Fu .................... A61N 1/0484 600/15 |
| 8,725,669 | B1 * | 5/2014 | Fu ....................... A61B 5/369 706/22 |
| 9,924,889 | B2 | 3/2018 | Navarro de Lara et al. |
| 11,055,356 | B2 * | 7/2021 | Ritchey ................ G06N 20/00 |
| 2016/0030762 | A1 * | 2/2016 | Glass .................... A61B 5/369 600/13 |

OTHER PUBLICATIONS

Abreu et al., "EEG-informed fMRI: A review of data analysis methods" Front. Hum. Neurosci. 12, 1-23 (2018).
(Continued)

*Primary Examiner* — Rochelle D Turchen
(74) *Attorney, Agent, or Firm* — QUARLES & BRADY LLP

(57) ABSTRACT

A system and method for integrated magnetic resonance imaging (MRI) and electroencephalogram (EEG) is described. The system includes an integrated radiofrequency (RF)-EEG cap that includes an EEG cap comprising a first layer of material containing a first plurality of holes that provide placeholders configured to receive EEG electrodes and an RF cap comprising a second layer of material containing a second plurality of holes and a plurality of RF coils fixed onto the second layer of material. The system also includes one or more fasteners configured to co-register the second plurality of holes to the first plurality of holes and to removably secure the RF cap to the EEG cap.

34 Claims, 14 Drawing Sheets

LAYER 1    LAYER 2    LAYER 3

(56) References Cited

OTHER PUBLICATIONS

Allen et al., A method for removing imaging artifact from continuous EEG recorded during functional MRI. Neuroimage (2000). doi:10.1006/nimg.2000.0599.

Angelone et al., Metallic Electrodes and Leads in Simultaneous EEG-MRI: Specific Absorption Rate (SAR) Simulation Studies. Bioelectromagnetics 25, 285-295 (2004).

Auerbach et al., "Multiband accelerated spin-echo echo planar imaging with reduced peak RF power using time-shifted RF pulses", Magn. Reson. Med. 69, 1261-7 (2013).

Barker et al., Non-invasive magnetic stimulation of the human cortex. Lancet 1, 1106-1107 (1985).

Bell et al., A primer on permanent and reversible interference techniques in animals for investigators of human neuropsychology. Neuropsychologia 115, 211-219 (2018).

Belliveau et al., "Functional mapping of the human visual cortex by magnetic resonance imaging", Science (80-.) 254, 716-719 (1991).

Bergmann et al., Combining non-invasive transcanial brain stimulation with neuroimaging and electrophysiology: Current approaches and future perspectives. Neuroimage 140, 4-19 (2016).

Bestmann et al., Functional MRI of the immediate impact of transcranial magnetic stimulation on cortical and subcortical motor circuits. Eur. J. Neurosci. 19, 1950-62 (2004).

Bestmann et al., Mapping casual interregional influences with concurrent TMS-fMRI. Exp. Brain Res. 191, 383-402 (2008).

Bestmann et al., On the synchronization of transcranial magnetic stimulation and functional echo-planar imaging. J. Magn. Reson. Imaging 17, 309-16 (2003).

Bohning et al., A Combined TMS/fMRI Study of Intensity-Dependent TMS Over Motor Cortex. Biol. Psychiatry 45, 385-394 (1999).

Bohning et al., Echoplanar BOLD fMRI of brain activation induced by concurrent transcranial magnetic stimulation. Invest Radiol 33, 336-340 (1998).

Bonmassar et al., Spatiotemporal brain imaging of visual-evoked activity using interleaved EEG and fMRI recordings, Neuroimage 13, 1035-1043 (2001).

Bungert et al., Reducing image artifacts in concurrent TMS/fMRI by passive shimming. Neuroimage 59, 2167-74 (2012).

Corea et al., Screen-printed flexible MRI receive coils. Nat. Commun. 7, 1-7 (2016).

Dale et al., Dynamic statistical parametric mapping: Combining fMRI and MEG for high-resolution imaging of cortical activity. Neuron (2000). doi: 10.1016/S0896-6273(00)81138-1.

Dale et al., Improved localization of corticla activity by combining EEG and MEG with MRI cortical surface reconstruction: A linear approach. J. Cogn. Neurosci. (1993). doi: 10.1162/jocn.1993.5.2.162.

Delorme et al., (2004) EEGLAB: an open source toolbox for analysis of single-trial EEG dynamics (pdf, 0.7 MB) Journal of Neuroscience Methods, 134:9-21.

Faller et al., An EEG-fMRI-TMS instrument to investigate BOLD response to EEG guided stimulation. Int. IEEE/EMBS Conf. Neural Eng. NER2019-March, 1054-1057 (2019).

Fox et al., "Efficacy of Transcranial Magnetic Stimulation Targets for Depression Is Related to Intrinsic Functional Connectivity with the Su bgenual Cingualate", BPS 72, 595-603 (2012).

Frass-Kriegl et al., Multi-turn multi-gap transmission line resonators—Concept, design and first implementation at 4.7T and 7T. J. Magn. Reson. 273, 65-72 (2016).

Fultz et al., Coupled electrophysiological, hemodynamic, and cerebrospinal fluid oscillations in human sleep. Science (80-.). 366, 628-631 (2019).

Goldman et al., Aquiring simultaneous EEG and functional MRI. Clin. Neurophysiol. 111, 1974-1980 (2000).

Gonord et al., Parallel-plate split-conductor surface coil: analysis and desig. Magn. Reson. Med. 6, 353-358 (1988).

Gotman et al., Combining EEG and fMRI in epilepsy: Methodological challenges and clinical results. J. Clin. Neurophysiol. 21, 229-240 (2004).

Griswold et al., Generalized autocalibrating partially parallel acquisitions (GRAPPA). Magn. Reson. Med. 47, 1202-10 (2002).

Hamalainen et al., Interpreting magnetic fields of the brain: minimum norm estimates. Med. Biol. Eng. Comput. (1994). doi:10.1007/BF02512476.

Hebb et al., Creating the Feedback Loop. Closed-Loop Neurostimulation. Neurosurg. Clin. N. Am.25, 187-204 (2014).

Herrmann et al., Simultaneous recording of EEG and BOLD responses: A historical perspective. Int. J. Psychophysiol. 67, 161-168 (2008).

Jacobs et al., Brain Oscillations Control Timing of Single-Neuron Activity in Humans. 27, 3839-3844 (2007).

Kearney-Ramos et al., Gray and white matter integrity influence TMS signal propagation: A multimodal evaluation in cocaine-dependent individuals. Sci. Rep. 8, 1-11 (2018).

Keil et al., "A 64-channel 3T array coil for accelerated brain MRI", Magn. Reson. Med. 70, 248-258 (2013).

Laistler et al., Handy magnetic resonance coils. Nat. Biomed. Eng. 2, 557-558 (2018).

Maravilla et al., "Transmission Line Receiver Coils (TLCs) for MRI", Proc. Intl. Soc. Mag. Reson. Med. 30 (2022).

Maravilla et al., "Twisted-Pair Receiver Coils for a Combined TMS/EEG/fMRI System", (2022).

Maris et al., Diverse Phase Relations among Neuronal Rhythms and Their Potential Function. Trends Neurosci. 39, 86-99 (2016).

Michel et al., Towards the utilization of EEG as a brain imaging tool. Neuroimage 61, 371-385 (2012).

Navarro de Lara et al., Evaluation of RF interactions between a 3T birdcage transmit coil and transcranial magnetic stimulation coils using a realistically shaped head phantom. Magn. Reson. Med. 84, 1061-1075 (2020).

Navarro de Lara et al., A novel coil array for combined TMS/fMRI experiments at 3 T. Magn. Reson. Med. 74, 1492-1501 (2015).

Niazy et al., Removal of FMRI environment artifacts from EEG data using opimal basis sets, Neuroimage, vol. 28, Iss. 3, 2005, pp. 720-737.

Nordmeyer-Massner et al., Stretchable coil arrays: Application to knee imaging under varying flexion angles. Magn. Reson. Med. 67, 872-879 (2012).

Noth et al., Simultaneous electroencephalography-functional MRI at 3 T: An analysis of safety risks imposed by performing anatomical reference scans with the EEG equipment in place. J. Magn. Reson. Imaging 35, 561-571 (2012).

Obermann et al., "Optimization and miniaturization of Rx-only coaxial coil interfacing", Proc. 28th Ann. Meet. ISMRM, Virtual, 2020.

Obermann et al., Ultra-flexible and light-weight 3-channel coaxial transmission line resonator receive only coil array for 3T. Proc. 27th Annu. Meet. ISMRM, Montreal, Canada 2018-2019 (2019).

Ogawa et al., "Brain magnetic resonance imaging with contrast dependent on blood oxygenation," Proc. Natl. Acad. Sci 87, 98-68-9872 (1990).

Opitz et al., "An integrated framework fro targeting functional networks via transcranial magnetic stimulation", Neuroimage 127, 86-96 (2016).

Ou et al., Multimodal functional imaging using fMRI-informed regional EEG/MEG source estimation. Neuroimage 52, 97-108 (2010).

Parastargeizabadi et al., Advances in closed-loop deep brain stimulation devices. J. Neuroeng. Rehabil. 14, 79 (2017).

Pascual-Leone et al., Transcranial magnetic stimulation in cognitive neuroscience virtual lesion, chronometry, and functional connectivity. Curr. Opin. Neurobiol. 10, 232-237 (2000).

Pascual-Leone et al., Transcranial magnetic stimulation: Studying the brain-behaviour relationship by induction of 'virtual lesions'. Philos. Trans. R. Soc. B Biol. Sci: 354, 1229-1238 (1999).

Paulson et al., "Cerebrovascular and brain metabolism reviews" (1990). doi: 10.1161/01.str.15.3.413.

(56) References Cited

OTHER PUBLICATIONS

Peters et al., Concurrent human TMS-EEG-fMRI enables monitoring of oscillatory brain state-dependent gating of cortico-subcortical network activity. Commun. Biol. 3, 1-11 (2020).
Peters et al., On the feasibility of concurrent human TMS-EEG-fMRI measurements. J. Neurophysiol. 109, 1214-1227 (2013).
Polimeni et al., "Reducing sensitvity losses due to respiration and motion in accelerated echo planar imaging by reordering the autocalibration data acquisition", Magn. Reson. Med. 75, 665-679 (2016).
Price et al., "The use of background EEG activity to determine stimulus timing as a means of improving rTMS efficacy in the treatment of depression: A controlled comparison with standard techniques", Brain Stimul. 3, 140-152 (2010).
Pruessmann et al., SENSE: sensitivity encoding for fast MRI. Magn. Reson. Med. 42, 952-62 (1999).
Robson et al., Comprehensive quantification of signal-to-noise ratio and g-factor for image-based and k-space-based parallel imaging reconstructions. Magn. Reson. Med. 60, 895-907 (2008).
Rossi et al., Safety, ethical considerations, and application guidelines for the use of transcranial magnetic stimulation in clinical practice and research. Clin. Neurophysiol. 120, 2008-2039 (2009).
Ruff et al., Combining TMS and fMRI. 45, 1043-1049 (2009).
Ruytenberg et al., "Shielded—coaxial—cable coils as receive and transceive array elements for 7T human MRI", 1-12 (2019).
Sack et al., Imaging the brain activity changes underlying impaired visuospatial judgements: simultaneous FMRI, TMS, and behavioral studies. Cereb. Cortex 17, 2841-52 (2007).
Sauseng et al., Neuroscience and Biobehavioral Reviews What does phase information of oscillatory brain activity tell us about cognitive processes? 32, 1001-1013 (2008).
Setsompop et al., "Blipped-controlled aliasing in parallel imaging for simultaneous multislice echo planar imaging with reduced g-factor penalty", Magn. Reson. Med. 67, 1240-1224 (2012).
Setsompop et al., High-flip-angle slice-selective parallel RF transmission with 8 channels at 7T. J. Magn. Reson. 195, 76-84 (2008).
Shirinpour et al., Experimental evaluation of methods for real-time EEG phase-specific transcranial magnetic stimulation. J. Neural Eng. 17, (2021).
Siebner et al., Consensus paper: combining transcranial stimulation with neuroimaging. Brain Stimul 2, 58-80 (2009).
Steyrl et al., Online Reduction of Artifacts in EEG of Simultaneous EEG-fMRI Using Reference Layer Adaptive Filtering (RLAF). Brain Topogr. (2018). doi:10.1007/s10548-017-0606-7.
Thut et al., The Functional Importanceof Rhythmic Activity in the Brain Minireview. Curr. Biol. 22, R658-R663 (2012).
Uutela et al., Visualization of magnetoencephalographic data using minimum current estimates. Neuroimage (1999). doi: 10.1006/nimg.1999.0454.
Van Audekerkea et al., Special designed RF-antenna with integrated non-invasive carbon electrodes for simultaneous magnetic resonance imaging and electroencephalography acquisition at 7T. Magn. Reson. Imaging 18, 887-891 (2000).
Van der Kouwe et al., Brain morphometry with multiecho MPRAGE. Neuroimage 40, 559-569 (2008).
Wang et al., Magnetic source imaging based on the Minimum-Norm Least-Squares Inverse. Brain Topogr. (1993), doi: 10.1007/BF01128692.
Weiskopf et al., Image artifacts in concurrent transcranial magnetic stimultion (TMS) and fMRI caused by leakage currents: modeling and compensation. J. Magn. Reson. Imaging 29, 1211-7 (2009).
Wiggins et al., 32-channel 3 Tesla receive-only phased-array head coil with soccer-ball element geometry. Magn. Reson. Med. 56, 216-223 (2006).
Willie et al., "Integrative regulation of human brain blood flow", Journal of Physiology (2014). doi: 10.113/jphysiol.2013.268953.
Zhang et al., "A high-impedance detector-array glove for magnetic resonance imaging of the hand", Nat. Biomed. Eng. 2, 570-577 (2018).
Zhang et al., Novel Flexible Electro-textile 3T MRI RF Coil Array for Carotid Artery Imaging: Design, Characterization and Prototyping. IEEE Trans. Antennas Propag. 67, 5115-5125 (2019).
Zrenner et al., Brain Stimulation Brain oscillation-synchronized stimulation of the left dorsolateral prefrontal cortex in depression using real-time EEG-triggered TMS. Brain Stimul. 13, 197-205 (2020).
Zrenner et al., Brain Stimulation Real-time EEG-defined excitability states determine efficacy of TMS-induced plasticity in human motor cortex. Brain Stimul. 11, 374-389 (2018).
Zrenner et al., Closed-loop neuroscience and non-invasive brain stimulation: A tale of two loops. Front. Cell. Neurosci. 10, 1-7 (2016).
Woletz et al., TMS Target tracking in TMS-fMRI experiments in 24th Annual Meeting of the Organization or Human Brain Mapping 12, 2-5 (2018).

* cited by examiner

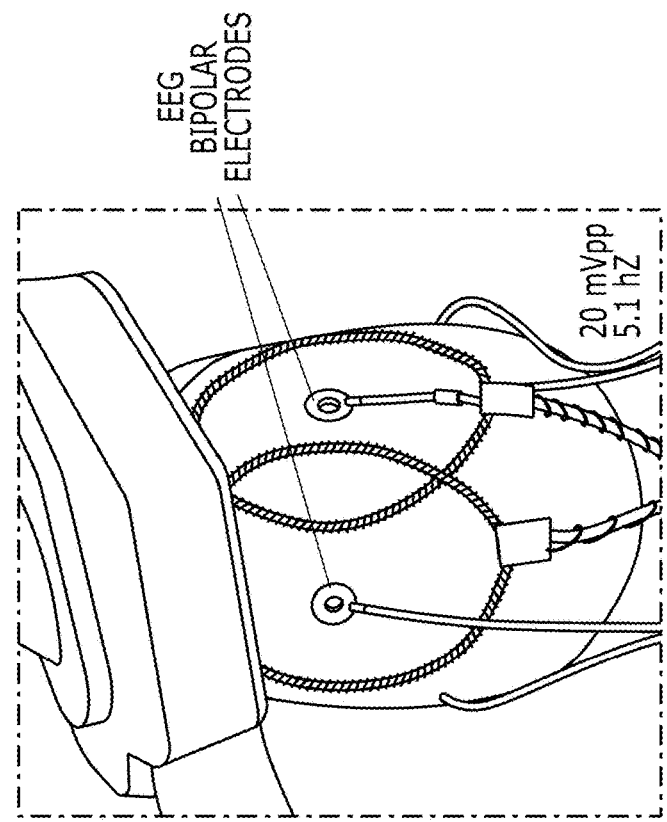
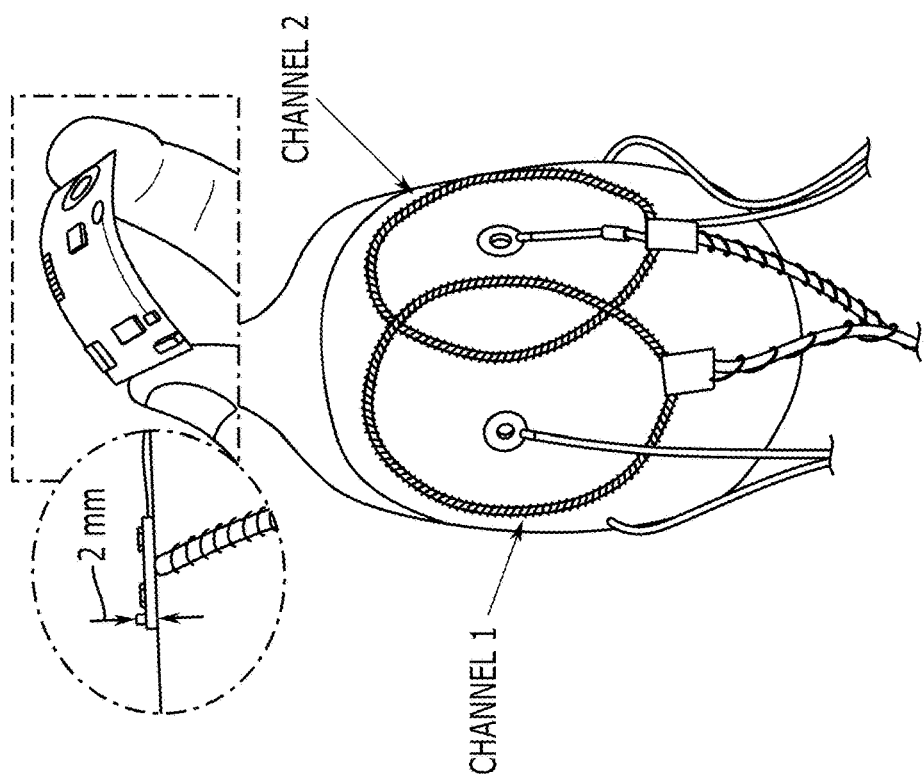
FIG. 3B
FIG. 3A

SYSTEM AND METHOD FOR INTEGRATED MAGNETIC RESONANCE IMAGING (MRI) AND ELECTROENCEPHALOGRAM (EEG)

CROSS-REFERENCE TO RELATED APPLICATIONS

This application is based on and claims priority to U.S. Provisional Patent Application No. 63/336,596, filed on Apr. 29, 2022, the entire contents of which is incorporated herein by reference.

STATEMENT REGARDING FEDERALLY SPONSORED RESEARCH

N/A

BACKGROUND

Functional magnetic resonance imaging (fMRI) provides an indirect measure of neuronal activity with high spatial resolution but suffers from low temporal resolution. Electroencephalography (EEG) is another non-invasive technique that records synchronous activity of large groups of neurons with millisecond temporal resolution. However, EEG lacks high spatial resolution and the ability to measure activity from deep brain structures. Thus, there is great interest in integrating EEG with fMRI for multimodal neuroimaging with high spatial and temporal resolution. Moreover, transcranial magnetic stimulation (TMS) is a non-invasive method of brain stimulation that provides a diagnostic and treatment tool in neurology and psychiatry. Practical solutions for combining fMRI, EEG, and TMS are lacking, and current implementations achieve low sensitivity of the radiofrequency (RF) coil, incomplete brain coverage, or both.

One substantial challenge to integrating one or more monitoring or stimulations systems with the use of MRI-based monitoring is that MRI interacts with any coils or any ferromagnetic materials placed within the imaging bore. When integrating, for example, fMRI with TMS, the RF coil arrays used for fast fMRI acquisition and the TMS coil must both be placed in close proximity of the head for optimal operation. This means that the TMS coil must be MRI compatible and accommodate the RF coils of the MRI system, which limits the usability of state-of-the-art rigid imaging helmets. Moreover, conventional setups are uncomfortable, which makes their use challenging, especially for subjects with claustrophobia or anxiety. These challenges are compounded when adding EEG or other monitoring systems along with TMS into the MRI-environment.

Thus, there is a need for systems and methods for delivering the requisite spatial and temporal information required by clinicians to effectuate monitoring and deploying therapeutic devices.

SUMMARY OF THE DISCLOSURE

The present disclosure addresses the aforementioned drawbacks by providing a system and method for integrated magnetic resonance imaging (MRI) and electroencephalogram (EEG). The system can include a wearable integrated radiofrequency (RF)-EEG cap that is compatible with transcranial magnetic stimulation (TMS).

In some aspects, the present disclosure provides an integrated brain-mapping system for the simultaneous acquisition of MRI, including functional MRI (fMRI), and EEG data. The RF-EEG cap includes a wearable EEG cap made of a first layer of material that includes a set of holes. The holes provide placeholders that can receive EEG electrodes in use. The RF-EEG cap further includes a wearable RF cap of a second layer of material. The second layer includes a second set of holes that can align with the first set of holes in use. The RF cap also includes several RF coils that can be fixed onto the second layer of material. The RF coils may be flexible coaxial RF elements, such as self-resonant flexible coils, that can form to the cap or the head of the subject while maintaining high performance. The RF-EEG cap also includes one or more fasteners that can be used to co-register the first and second sets of holes so that they align when placed on the head of the patient. The fasteners can also be used to removably secure the EEG cap and RF cap for integrated use. The system may further include a TMS coil or a TMS coil array. The RF-EEG cap may be compatible with TMS as its thin design allows for unobstructed placement of a TMS coil array and close proximity to the scalp to achieve stimulation of the brain with high efficiency.

In another aspect of the disclosure, a method is provided for causal functional brain mapping of a subject. The method allows for concurrent MRI, EEG, and TMS. A wearable RF-EEG cap may be placed on the head of a subject, and EEG electrodes may be positioned on the scalp of the subject using the holes in the RF-EEG cap as placeholders. The TMS coil or TMS coil array may be positioned over the head of the subject outside of the RF-EEG cap. With this setup, causal functional brain mapping may be performed by acquiring MRI data and EEG data. The MRI data may be acquired by performing a desired pulse sequence using an MRI system and the RF coils of the RF cap. MRI acquisition may include fMRI and parallel imaging. The EEG data may be simultaneously acquired using the EEG electrodes. TMS may be applied at a trigger time, and the response may be measured by MRI and EEG to determine localized TMS-elicited brain responses. The MRI data, EEG data, or some combination thereof may be used to determine a trigger time for TMS application. The MRI and EEG data may also be used to determine the placement of the TMS coil or TMS coil array elements.

These are but a few, non-limiting examples of aspects of the present disclosures. Other features, aspects and implementation details will be described hereinafter.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 3A shows an example RF-EEG cap in accordance with some aspects of the present disclosure.

FIG. 3B shows an example brain mapping system, including the example RF-EEG cap of FIG. 3A and a TMS coil, in accordance with some aspects of the present disclosure.

DETAILED DESCRIPTION

Figure 1:
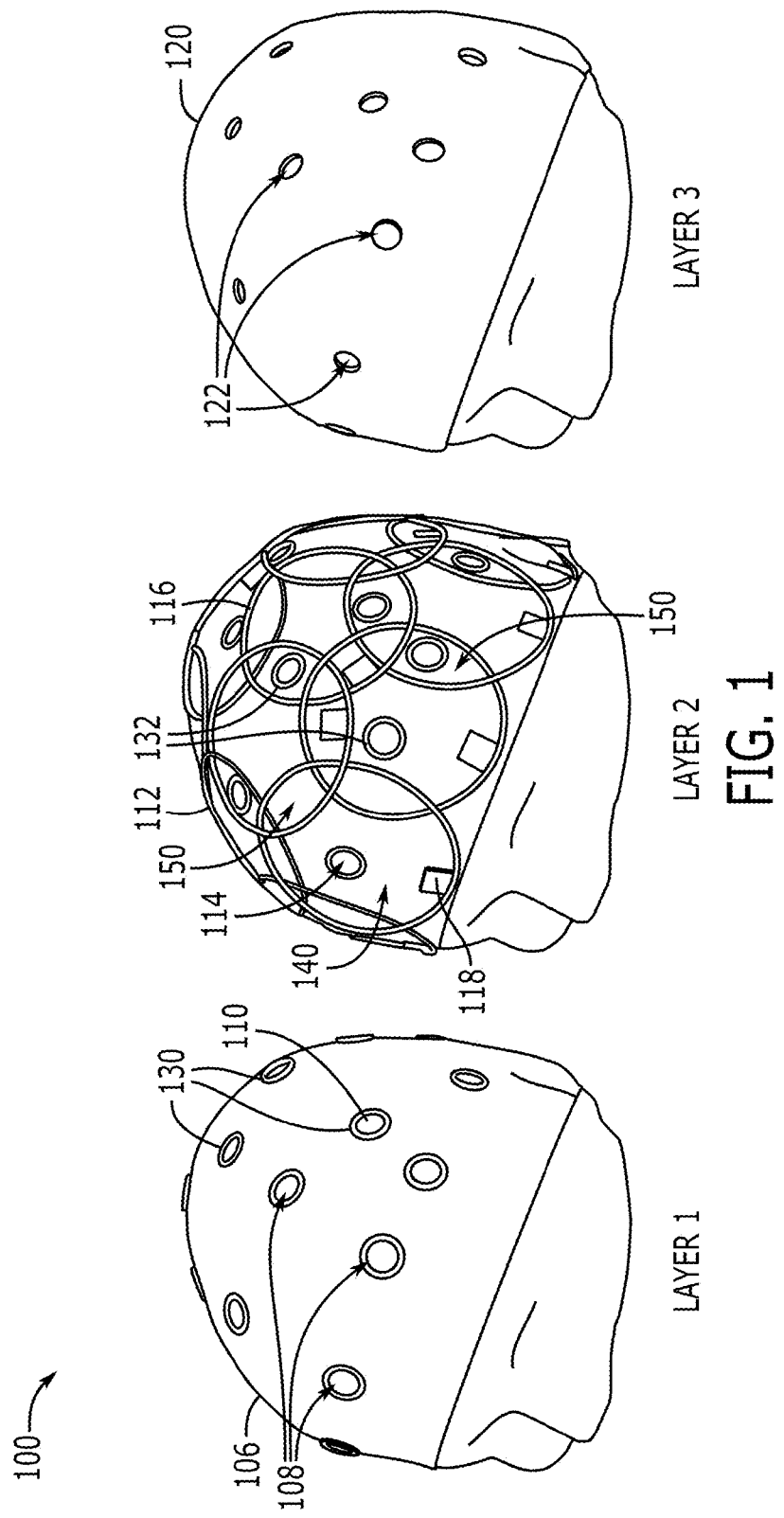
FIG. 1 illustrates an example RF-EEG cap in accordance with some aspects of the present disclosure.

Before any aspects of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Functional magnetic resonance imaging (fMRI) is a widely used method for non-invasive mapping of brain activity. It reveals the whole-brain hemodynamic response to tasks or stimuli with millimeter spatial resolution based on the BOLD effect. fMRI provides an indirect measure of neuronal activity that is characterized by the underlying neurovascular coupling mechanism. Although the peak of the hemodynamic response occurs several seconds after the stimulus, recent investigations of hemodynamic and vasodynamic responses show that fMRI may reveal much more detailed information of underlying neuronal activity than previously believed. To practically achieve the higher specificity for fMRI experiments, high-density RF coil arrays are the key enabling technology for fast acquisition methods that are needed to increase the spatial and the temporal resolution while maintaining adequate signal-to-noise ratio (SNR).

Electroencephalography (EEG) is a non-invasive neurophysiological technique, which measures signals that reflect the summation of postsynaptic potentials of relatively large groups of neurons firing synchronously. This synchronous activity can be monitored with millisecond temporal resolution allowing accurate tracking of the rapidly changing electrical dynamics of neuronal populations. As the recording electrodes are placed on the scalp, the task of localizing the underlying neuronal sources is non-trivial. Because the number of 'possible source configurations' is typically much larger than the number of sensors, a priori assumptions/constraints need to be incorporated. Therefore, the spatial resolution of EEG is relatively low and the capability of record neural activity from deep brain structures is limited, which has resulted in a great interest in integrating EEG with fMRI to a multimodal neuroimaging technique with millimeter spatial and millisecond temporal resolution.

Transcranial magnetic stimulation (TMS) is a non-invasive brain stimulation method that has shown great success as a diagnostic, prognostic and treatment tool in clinical neurology and psychiatry. A particularly well-known application is the treatment of drug-resistant major depression with repetitive TMS (rTMS), which was FDA approved in 2008. Apart from clinical applications, TMS has become a transformative tool in many fields of cognitive neuroscience due to the fact that it enables incorporation of a causal dimension to the experiments. Indeed, TMS has the unique capability to interact safely with a well-defined cortical region to create a form of a reversible 'virtual lesion' that can be used to map causal relationships between the stimulated brain area and the observed behavior, somewhat analogously to the classical lesion studies in animals.

The triple combination of TMS with fMRI and EEG simultaneously presents technological challenges. First, even though the feasibility of concurrent TMS/fMRI experiments has been well documented, practical easy-to-use implementation still poses several technological challenges and trade-offs. In the conventional setup for concurrent TMS/fMRI, the MR compatible TMS coil is mounted inside a large-volume head coil. The main drawbacks of this type of setup are the inferior sensitivity compared to, for example, the typical 32/64-channel head coils and the constraints in the TMS coil placement. Thus, a high sensitivity RF coil array with full brain coverage that allows concurrent TMS is still lacking.

Second, while the combination of fMRI/EEG has been proven to be feasible and safe, very little efforts have been made to integrate EEG sensors and RF receive coils to combine the two techniques in the best possible way. One significant issue for combined EEG/fMRI is that the current setups are less than ideal in terms of the comfort. In particular, adding an EEG cap into the already limited space of the RF coil helmet increases the discomfort during the scans, which is particularly problematic for subjects with claustrophobia or anxiety. On a related note, certain new approaches such as sleep fMRI/EEG studies would greatly benefit from the increased comfort levels in the experiments that last several hours.

The present disclosure provides systems and methods that overcome these drawbacks and integrates magnetic resonance imaging (MRI) and electroencephalography (EEG) systems. Moreover, the systems and methods described herein can be utilized with concurrent TMS administration with MRI and EEG exams. Such high quality multimodal TMS/EEG/fMRI neuroimaging data acquisition combines the high spatial resolution of fMRI with the millisecond-level temporal resolution of EEG to provide the spatiotemporal precision needed for noninvasive causal brain mapping in response to TMS. The system and methods allow for full brain coverage in a controlled fashion, including neuronavigation methods for coil placement and tracking inside the MR environment, high coil sensitivity across a multi-channel design, and shorter acquisition times utilizing parallel imaging methods. Such whole-brain coverage allows for MRI and EEG characterization of the entire brain of a participant.

Many neurological and psychiatric illnesses are considered disorders of brain circuits. The treatment strategies seek to modulate the dysfunctional brain circuits to relieve the symptoms. Brain stimulation methods have shown promising therapeutical effects by manipulating the affected brain circuits for conditions such as MDD and OCD. There is mounting evidence that the effects of the stimulation and therefore the efficacy of the treatment depend on the primary stimulation target region as well as its network-level connectivity pattern (i.e., spatial dependency). Additionally, the neuromodulation effects depend also on the brain state at the time of stimulation (i.e., time dependency) usually defined by neural oscillations.

Certain stimulation devices have been developed to enable closed loop operation in which the timing, magnitude and other stimulation parameters are determined based on a feedback signal. Such closed loop systems have been introduced for deep brain stimulators (DBS) with the benefit of having a less disruptive impact on cognitive processes that depend on coordinated neural oscillations. For non-invasive brain stimulation methods like TMS, closed loop applications have also been proposed that could be used ultimately to optimize individualized therapeutic treatments. In these applications, the TMS protocol is time-locked to a quantitative brain state biomarker, such as the EEG spectral power at a specified frequency band or to the negative EEG peak of instantaneous alpha oscillations. Acquiring fMRI data concurrently with EEG during these closed loop applications for TMS can allow for precise monitoring and recording of the propagation of TMS-induced activations across the brain networks including therapeutically important deep brain structures. The high-quality spatiotemporal data acquired can be leveraged to understand the network-level mechanisms of action for TMS and to optimize the TMS treatment outcome for individuals.

Referring, now to FIG. 1, an integrated wearable RF-EEG cap 100 for use with an integrated brain-mapping system to achieve simultaneous MRI and EEG is illustrated. The wearable RF-EEG cap 100 may include three layers: an EEG cap 106 layer, an RF cap 112 layer and a cover 120 layer. The three layers may be removably fastened together by one or more fasteners. Each of the layers can contain through holes that are co-registered when the layers are fastened together.

The wearable RF-EEG cap 100 may have a modular design in which the three layers are separable and the EEG cap 106 and RF cap 112 can function independently. This modular design promotes cost-effective fabrication and ease-of-use as the RF coil components can be easily removed from the EEG cap for cleaning and maintenance. The wearable design of the RF-EEG cap may allow for unrestricted and close positioning of the TMS coil or TMS coil array across the entire scalp, allowing for complete compatibility with TMS and efficiency of the brain stimulation. The wearable RF-EEG cap 100 may be constructed in various sizes to fit a wide range of heads of participants. Additionally or alternatively, the wearable RF-EEG cap 100 may be uniquely fabricated to optimally fit the head of a specified subject.

Furthermore, both the flexible RF cap and the EEG cap can be used independently for control experiments if desired. Additionally, the total thickness of the integrated RF-EEG cap can be thin for patient comfort and to ensure efficient TMS stimulation across the entire head. Preferably, the thickness of the RF cap can be 5 mm or less, which can maintain the loss of TMS coil efficiency to 10%. However, the thickness of the RF cap may alternatively be constrained to 30 mm, 20 mm, 10 mm, 2 mm or another thin thickness that facilitates close placement of a TMS coil, for example.

The RF-EEG cap 100 may include a first layer that makes up a wearable EEG cap 106. The EEG cap 106 can be constructed from a flexible or soft material, such as fabric, leather, synthetic leather, or the like. The EEG cap may be configured with one or more through holes 108 that act as placeholders for EEG electrodes. In use, EEG leads or cables can be routed along the EEG cap, and the EEG electrodes may be placed in the holes 108 onto the scalp 110 of a subject. The EEG leads may be individually routed to reach the holes 108 for electrode placement or may be twisted together to minimize induction of voltage within the MRI system, for example.

The EEG cap 106 may include any number of holes 108 to facilitate the desired coverage and spatial pattern for EEG electrode placement while balancing system complexity. As standard MR-compatible EEG amplifiers are typically available as 32-channel modules, the EEG cap 106 may include 32 holes 108 for EEG electrodes. The holes 108 may be distributed in any of a variety of patterns on the EEG cap 106. For example, they may be distributed based on the standard approach for a 32-channel EEG system. They may also be randomly distributed, pseudo-randomly distributed, equally distributed, distributed using a Poisson disk distribution, or the like. The positions of the holes 108 may also be determined based on the positions of RF coils, which will be described in further detail below. The holes 108 may be of any suitable shape, such as circular, round, elliptical, polygonal, or the like and may be sized to fit EEG electrodes.

The EEG cap 106 may also include a first set of grommets 130 or eyelets around the inner perimeter of each of the holes 108. The grommets 130 may be made of plastic, rubber, leather, synthetic leather, fabric, non-ferrous metal, polymer, ceramic, another MR-safe material, or a combination thereof. The grommets 130 may be round, circular, elliptical, polygonal, or of another suitable shape that may match the shape of the holes 108. The grommets 130 may include a collar that provides reinforcement of the first layer of material. The collars may have substantially similar shape as the grommets 130 or holes 108 or may have another shape such that the thickness of the collar is variable. The collar may also facilitate threading of EEG electrodes, cables, or the like through the holes 108. The grommets 130 may be used to facilitate the alignment of the EEG cap 106 with the RF cap 112 such that the holes are co-registered when the caps are integrated, which will be described in further detail below.

Each of the grommets 130 may be fashioned from a single piece secured to the layer of material. For example, the collar may be crimped around the layer of material to secure the grommet 130 to the EEG cap 106. The grommets 130 may alternatively be fashioned from two pieces, wherein each of the pieces is inserted into a hole 108 from a respective side of the layer of material. The two pieces may be fastened together to sandwich a part of the layer of material to secure the grommet 130 to the layer of material within the hole 108.

The grommets 130 may also be configured to removably or permanently fasten the EEG cap 106 to other layers of the RF-EEG cap 100, as will be described further below. For example, each of the grommets 130 on the EEG cap may also have a neck portion or protrusion that forms a snap or other fastener in conjunction with another grommet. Each grommet 130 may alternatively or additionally have a recess that receives a protrusion of another grommet.

The RF-EEG cap 100 may further include a second layer that provides a wearable RF cap 112. The RF cap 112 may be constructed from a soft or flexible material, such as fabric, that is configured with a second set of through holes 114. The RF cap 112 may be formed from an electrical insulator to isolate the electronic components. The RF cap 112 may additionally or alternatively include one or more layers of electrically insulating material. The holes 114 may be circular, elliptical, polygonal, or another shape. The holes 114 may have the same shape and size of the corresponding holes 108 of the EEG cap 106, or they may have different shapes and sizes. The holes 114 may be positioned to align with the holes 108 of the EEG cap 106 when the EEG cap 106 and RF cap 112 are both placed on the head of a subject. The holes 108 and 114 may axially align fully, for example, if the holes 108 and 114 are of the same shape and size. The holes 108 and 114 may also align by aligning the center of the holes 108 and 114. They may alternatively align partially such that the overlapping area of the holes 108 and 114 is large enough to receive an EEG electrode.

Each of the second set of through holes 114 may include a grommet 132 that lines the inner perimeter of the hole 114. Like the first set of grommets 130, the second set of grommets 132 may provide reinforcement of the perimeters of the holes 114, facilitate threading of EEG electrodes through the holes 114 of the RF cap 112, or facilitate alignment of the RF cap 112 to the EEG cap 106 such that the through holes 108 and 114 co-register when the caps are used together.

The second set of grommets 132 may have substantially similar properties as those of the first set of grommets 130 as described above. The second set of grommets may also be different than the first set of grommets 130. For example, the grommets may have collars of different thicknesses or shapes, be made of different material, be constructed from a different number of pieces, or the like as compared to the first set of grommets 130.

The RF cap 112 may be removably fastened to an EEG cap 106 using any suitable fastener, such as snap fasteners, zippers, buttons, pins, clips, hook and loop tape (e.g. Velcro), ties, hook and eyes, buckles, permanent or removable adhesive, permanent or removable glue, sewn stiches, or the like. For example, a first part of a fastener may be secured to the outer surface of the EEG cap 106, and a second part of a fastener may be secured to the inner surface of the RF cap 112 in order to removably or permanently secure the EEG cap 106 and RF cap 112 together. The fasteners may be positioned such that the holes 114 of the RF cap 112 align axially with the holes 108 of the EEG cap 106 when the two caps are fastened together for use.

Additionally or alternatively, the first set of grommets 130 and the second set of grommets 132 can act together to form fasteners to removably or permanently secure the EEG cap 106 with the RF cap 112. For example, the grommets 130 and 132 can form a snap fastener. The first grommet 130 may include a protrusion that can be received by a recess of the second grommet 132 to removably secure the first grommet 130 and second grommet 132 together. Similarly, the first grommet 130 may include a recess to removably receive a protrusion of the second grommet 132.

As another non-limiting example, the first grommet 130 may include a neck that may be received by a second grommet 132. The neck may surround the entire perimeter of the grommet 130 or a partial perimeter of the grommet 130. The neck may have a slightly smaller diameter, width, or size as the second grommet 132 to fit into the hole 114 to facilitate easy alignment of the holes 108 and 114. The neck may alternatively have the same size as the holes 114 and resiliently compress such that it can be inserted into the hole 114. After inserting the compressed neck, it can be relaxed to create pressure between the neck and the receiving grommet 132 to secure the caps together. Similarly, the second grommet 132 may include a neck that may be received by the first grommet 130. The neck may include one or more outward facing protrusions to couple the grommet 130 or 132 with the complimentary grommet 132 or 130, respectively.

As another nonlimiting example, after aligning the holes 108 and 114, the holes 108 and 114 or grommets 130 and 132 can receive flexible O-rings or gaskets. The O-rings can be compressed to fit into the holes 108 and 114 and subsequently be relaxed to couple the EEG cap 106 and RF cap 112 together. The O-rings may have outward collars on each end to prevent movement through the holes 108 and 114 after placement.

The holes 114 may provide access to the scalp 110 for the EEG electrodes while the RF cap 112 is situated on the EEG cap 106. The RF cap 112 may also include several RF coils 116. The RF coils 116 may be arranged around the holes 114, such that they do not obscure the holes 114 for placement of EEG electrodes when the cap is in use.

The RF coils 116 may be constructed from flexible coaxial cables or other flexible conductors that can be attached to soft materials, like the RF cap 112, and wrapped around surfaces of arbitrary curvature, such as a head of a subject. The RF coils 116 may be sewed onto or otherwise attached to the RF cap 112. The RF coils 116 may be self-resonant coil elements. Advantageously, the self-resonant flexible coaxial RF elements can maintain SNR when stretched or bent. The RF coils 116 may also be constructed from twisted pairs, liquid metal flexible elements, other flexible coils, or other RF coil technologies. Furthermore, the RF coils 116 may be overlapping to achieve geometric decoupling that reduces the mutual inductance between elements, which remains highly efficient even when the RF cap 112 is bent, enabling unimpaired parallel imaging performance.

The RF coils 116 may be evenly spaced over the entire RF cap 112 to provide full brain coverage for imaging. The RF coils 116 may be loop coils that have a center region 140. The holes 114 may be positioned in the center regions of the RF coils 116 in order for the RF coils 116 to not overlap the holes 114 and thereby the EEG electrodes.

As another non-limiting example, the RF coils 116 may be arranged in a soccer-ball pattern to provide optimal coil sensitivity profiles and facilitate parallel imaging. In the soccer-ball pattern, each RF coil 116 overlaps with several neighboring RF coils 116 that are positioned radially around it. For example, each RF coil 116 may be surrounded by 5 overlapping RF coils 116 that are evenly spaced radially around the center coil. This soccer-ball pattern can also facilitate placement of EEG electrodes. For example, through holes 114 can be placed at or near the center of one or more of the RF coils 116 in the center region 140. Additionally or alternatively, holes 114 may be placed at the center of or otherwise within the coil overlap regions 150. In this way, the EEG electrodes can be evenly spaced and avoid overlap with the RF coils 116. The holes 108 in the EEG cap 106 may have corresponding positions to align or co-register when the EEG cap 106 and RF cap 112 are integrated.

The RF coils 116 may be circular or elliptical loops or have other shapes. Other coil arrangements may be used to optimize image acquisition or to provide flexibility in the placement of EEG electrodes.

As one non-limiting example, the flexible coaxial RF elements may be constructed from a suitable flexible coaxial cable, such as Molex 047SC-2901. The RF coils 116 may include circuitry 118 that is used to transmit RF signals and can be used to tune and match the RF coils 116. To interface the RF elements to preamplifiers, the circuitry 118 may be connected via coaxial cables to an interface box that contains preamplifiers and a plug consistent with the MRI system. In this way, the circuitry 118 may be electrically connected to communicate RF electrical signals to or from the RF coil 116. Such signals may be produced by the RF coils 116 coupling with the MR signal from a subject wearing the RF cap 112. The signals may also include transmit signals provided by a control system to excite a volume for imaging. The RF coils 116 may include receive elements and be configured to receive RF signals with or without the integration of the EEG cap 106. The RF coils 116 may also include transmit elements or transceive elements and be configured to transmit or receive RF signals with or without the integration of the EEG cap 106.

The circuitry 118 may further include a PIN diode configured to actively detune the RF coil 116 during the RF transmission phase. To maintain a small thickness of the RF-EEG cap 100, the PIN diode may be thin. For example, the PIN diode may be limited to a thickness of <5 mm, <2 mm, or the like. The circuitry 118 may also include a fuse configured to block RF transmit power in the event the PIN diode fails. The circuitry 118 may be configured using a printed circuit board (PCB) designed from flexible substrate and miniaturized components to minimize the footprint of the circuitry 118.

The RF cap 112 may contain any number of RF coils 116 of various sizes to achieve a desired balance between anatomical coverage, parallel imaging capability, depth sensitivity, compatibility with MR systems, and overall system complexity. For example, the number of RF coils 116 can be chosen such that a single system plug is required for standard MRI systems. In a non-limiting example, 24 RF coils 116 may be used, which can achieve full anatomical coverage with high parallel imaging performance while balancing system complexity. The RF coils 116 may have any diameter from 1 cm-20 cm, with a preferred diameter greater than 5-6 cm, such as 8 cm, in order to maintain sensitivity to depths of deep brain structures.

Connecting the EEG cap 106 and RF cap 112 may maximize durability of the whole assembly. The RF cap 112 can also be removable from the EEG cap 106. This modular design facilitates maintenance, cleaning, and independent EEG and MRI experiments that may be used for experimental control. For example, the EEG cap 106 may be washed or sterilized between uses without introducing moisture to the RF cap 112 that may damage the electronics. Furthermore, with this design, the EEG cap 106 may be the only textile component having a direct contact with the subject's head.

The RF-EEG cap 100 may further include a third layer forming a cover 120 placed over the RF cap 112 layer to assure all electronic components are isolated from the subjects or the operators. The cover 120 may be removably fixed onto an outer surface of the RF cap 112, to facilitate maintenance on the RF coils 116, if necessary. The cover 120 may be constructed from medical synthetic leather to provide stability to the assembly, component protection of the RF coils 116, and electrical insulation for safety. With the cover 120, only the cables may be accessible by the user to be attached to interface boxes for the preamplifiers. The cover 120 may also contain holes 122 that align with the holes 114 of the RF cap 112 and the holes 108 of the EEG cap 106 to facilitate placement of EEG electrodes. As described in the context of the EEG cap 106 and RF cap 112, above, the holes 122 in the cover 120 may include grommets or fasteners to provide alignment with the RF cap 112 or to secure the cover 120 to the RF cap 112. The cover 120 may include other fasteners to removably or permanently couple the cover 120 to the RF cap 112.

The RF-EEG cap 100 can be assembled with an EEG system in which EEG leads are routed to the holes 202, and EEG electrodes are thread into the through holes 202 and placed onto the scalp of a subject. The EEG leads may be twisted together to form bundles of EEG cables to minimize voltage induce by RF pulses of the MRI system. The EEG leads may be routed on the sides of the head or in other desired paths. The EEG system may be a commercially available or custom system, including MR-safe EEG leads and electrodes. Integration of the EEG leads and electrodes may be monitored for safety. For example, a gradient eddy current heating test may be used. The temperature may be monitored to ensure that the change of temperature on the surface before and after running a defined sequence is within a given safety threshold, such as 4° C. Heating of the EEG electrodes and conducting leads may also be monitored, especially during RF transmission, and maintained under a safety threshold. For example, the temperature of the EEG electrodes, leads, cables, or the like may be monitored using optical sensor probes or other methods. The specific absorption rate (SAR) or power use may also be monitored using standard approaches, and MRI sequences with low flip angles may be used to reduce power deposition.

The EEG leads may connect to a control system by an electrical connection, such as wires facilitated by cables. The cables can connect an EEG amplifier to each of the EEG electrodes that are located within the RF coil area. The electrical connection may extend from the EEG electrodes and leads positioned in the EEG cap 106 to communicate EEG electrical signals received from a patient wearing the EEG cap. These cables may interfere with the RF elements causing decreased sensitivity. Thus, to minimize such effects, the cables may be optimally routed through a path of minimum electric field of the RF coils. Such path may be determined by characterizing the electric field by simulating or experimentally measuring the electric field of the RF coils. Using simulations, the placement of the RF coils may also be designed to provide a path of low electric field for the EEG cables.

Figure 2:
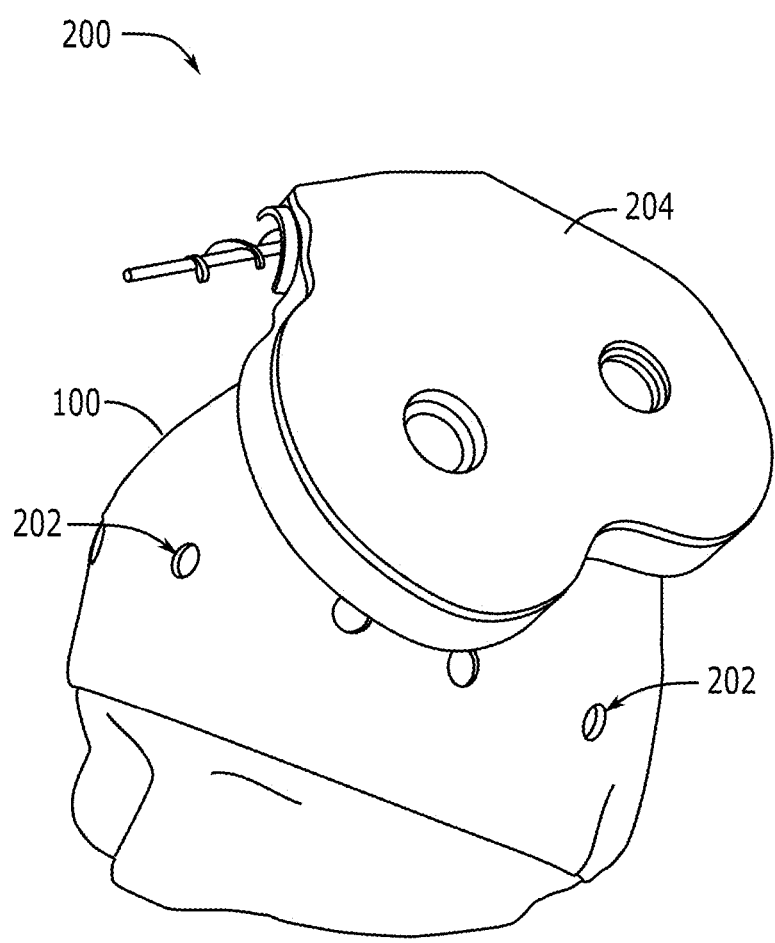
FIG. 2 illustrates the RF-EEG cap of FIG. 1 with an optional, integrated TMS coil to form an integrated brain mapping system 200 in accordance with some aspects of the present disclosure.

Referring now to FIG. 2, the RF-EEG cap 100 may be further integrated with a TMS coil 204 to form an integrated brain mapping system 200 that allows for multimodality imaging, including simultaneous MRI and EEG, with concurrent TMS. The MRI may include functional MRI (fMRI) as well as anatomical or quantitative imaging.

The stimulation system may include a single TMS coil 204 or may be a multi-channel TMS coil array that includes multiple TMS coils arranged in an array, as will be described below. Advantageously, the placement of the TMS coil 204 or TMS coil array may be unobstructed by the RF coils, due to the small thickness and close fit to the subject of the RF-EEG cap 100. The brain mapping system 200 may further include a neuronavigation system that facilitates precise placement of the TMS coil 204 or TMS coil array over the head of the subject. The neuronavigation system can allow the user to visualize and record the position of the TMS coil 204 or TMS coil array with respect to the brain anatomy. The neuronavigation system can also be used to plan the stimulation area using anatomical or functional MRI images or EEG data. The neuronavigation system may include a user interface that displays images of the subject along with the relative position of the TMS coil 204 or TMS coil array and the target of the stimulation. The user interface may also allow the user to select a region to target for TMS. The user interface may also display function data, such as fMRI data overlaid onto anatomical images, EEG time course data, stimuli time course data, or the like.

The RF-EEG cap 100 can be used for causal functional brain mapping using a combination of MRI, EEG, and TMS. The wearable RF-EEG cap 100 can be placed on the head of a subject, and EEG electrodes can be placed through the placeholders onto the subject's scalp. The subject may be placed in an MRI scanner wearing the RF-EEG cap, including an EEG cap 106, an RF cap 112, EEG leads, RF electrical connections, and EEG electrical connections. Using the RF coils 116, MRI data can be acquired with a variety of pulse sequences, which may include anatomical imaging data, fMRI data, quantitative MRI data, or other MRI data. The pulse sequences may include parallel imaging facilitated by the multi-channel RF array. While in the scanner, the MR-compatible EEG electrodes may be used to simultaneously acquire EEG data.

Further, a TMS coil or TMS coil array may be placed outside of the RF-EEG cap 100 over the head of the subject while inside the scanner. The thin fitting cap allows for unobstructed positioning of the TMS coil or TMS coil array for flexibility in choosing the stimulation target. The thin fitting cap also allows for close placement of the TMS coil or TMS coil array to achieve efficient stimulation of the brain.

The use of the TMS system, such as the coil or coil array location or stimulation timing, may be informed by the synchronization data acquired using the MRI or EEG systems. For example, the positioning of the TMS coil or TMS coil array may be informed by anatomical MRI images, fMRI data, the EEG time course data, or a combination thereof. For example, the TMS coil may be placed in close proximity to a desired brain structure identified by the anatomical MRI images. The placement may also be chosen to target a brain region involved in certain brain functions as identified by the fMRI or EEG data, for example. Once placed, the TMS can be applied at a trigger time that may be determined using the synchronization data, such as fMRI or other MRI data, the EEG time course data, or a combination thereof. For example, the trigger time may be defined based on or defined by a predefined phase of EEG oscillations or instantaneous EEG oscillations. For example, a predefined phase may include a peak, a trough or negative peak, or another phase defined relative to the amplitude or frequency or the instantaneous EEG oscillations. As a non-limiting example the trigger time may be defined as a trough detected on pre-defined instantaneous alpha oscillations. The trigger time may further be determined based on a pause time of the MRI pulse sequence. In this way, concurrent EEG, MRI, and TMS can be applied using a time course that may be determined by the user or determined by the acquired data. The TMS-elicited brain responses can be measured by the MRI and EEG data and stored and analyzed using a computer system.

The RF-EEG cap 100 significantly expands the spatiotemporal resolution of mapping the TMS-elicited brain responses across the entire brain. This enables causal studies by using TMS to disrupt or modulate the ongoing regional processing while recording the ensuing changes in electric and hemodynamic activity reflected in fMRI and EEG data. By applying multimodal data fusion techniques, the spatially precise fMRI activation maps can be used to reduce the ambiguity in the EEG source localization problem.

Closed loop experiments can be performed to elucidate the network of brain regions activated by the focal TMS. Such experiments may offer the possibility to investigate the temporal and spatial correlations of the stimulated cortical target region with the whole-brain networks that mediate the therapeutic effects through functional connectivity. Thus, the brain mapping system 200 can be used to optimize and individualize TMS treatment of mental health disorders, such as MDD, in the future.

EXAMPLES

Example 1—Prototype

To enable concurrent non-invasive stimulation (TMS) and whole-head multimodal imaging (EEG-fMRI), flexible RF coil technology is applied to build a first-of-its-kind TMS compatible integrated multimodal imaging array, called an RF-EEG cap. The proposed system allows unrestricted positioning of the TMS coil across the entire scalp. A 2-channel prototype was built and used to conduct a feasibility study analyzing the effects of a TMS coil and EEG-electrodes on the imaging quality (SNR and $B_0$ maps), the in-bore EEG data quality, and EPI time series stability. The results indicate that the flexible coaxial RF technology is a feasible choice to build the proposed RF-EEG cap.

A 2-channel "RF-EEG Cap" prototype for 3T was successfully built using flexible coaxial technology to allow concurrent TMS/fMRI/EEG applications. The effects on the SNR, $B_0$, EEG data quality, and EPI image quality were found minimal.

Introduction

There is mounting evidence that the effects of TMS and its therapeutic efficacy depend on the primary stimulation target region as well as its connectivity pattern (spatial dependency). Additionally, the neuromodulation effects depend on the brain state at the time of stimulation (time dependency) defined by neural oscillations. Combining TMS with fMRI and EEG offers the next-generation capabilities for causal functional mapping of the human brain circuits in a non-invasive way with unprecedented spatial and temporal resolution potentially enhancing therapeutic protocols through closed-loop applications. However, the triple combination presents technological challenges especially due to the lack of dedicated hardware to allow optimal performance of TMS and MRI.

Feasibility of concurrent human TMS/EEG/fMRI measurements at 3 T has been recently demonstrated. However, the presented data were acquired either with the body coil, which provides extremely low sensitivity, or a birdcage coil, which limits the placement of the TMS coil and does not support multichannel TMS coil arrays. Moreover, no parallel imaging acquisition methods were used due to the lack of multichannel RF coils, limiting the spatiotemporal resolution of the acquisition. Nevertheless, these results rigorously demonstrate the basic feasibility and safety of the technology.

The system provides the first-of-its-kind wearable RF-EEG cap to allow full-head coverage concurrent TMS/fMRI/EEG acquisition. A 2-channel prototype, shown in FIG. 3A, was constructed to assess the feasibility of the proposed RF-EEG cap.

Methods

Flexible coaxial RF elements, which are easily attachable to soft materials were used for the prototype construction. Two 8 cm diameter coils were built from flexible coaxial cable (Molex 047SC-2901, IL, USA) following proposed tuning/matching circuitry. Active detuning and preamplifier decoupling were implemented. Both elements were sewn onto a cloth cap and connected through 22.5 cm coaxial cables to an interface box containing one 3 T preamplifier (Siemens, Germany) and a 3 T Skyra plug. Placeholders for EEG-electrodes in the middle of each element were made on the cap to facilitate the positioning.

The prototype was tested on the bench using a VNA (Keysight Technologies, CA, USA) as: (i) stand-alone (only having RF elements), referred to as RF Cap; (ii) placing two bipolar MR compatible EEG-electrodes (Brain Products GmbH, Germany), referred to as RF-EEG Cap and (iii) placing the EEG-electrodes and a TMS coil (MRi B91, MagVenture, Denmark) over the cap, referred to as RF-EEGCap+TMS.

SNR maps and $B_0$ maps were used to evaluate the effects on the imaging of the two additional modalities. The SNR maps were acquired with FOV=256 mm, 1 slice, FA=30°, TR=9.1 ms, TE=4.8 ms, SL=2 mm, and 1 mm in-plane. The $B_0$ maps were acquired with FOV=220 mm, 18 slices, FA=75°, TR=300 ms, $TE_1$=5 ms, $TE_2$=7.46 ms, SL=5 mm, and 2.2 mm in-plane. SNR maps and $B_0$ maps were processed and analyzed with in-house MATLAB scripts for visualization.

Additionally, to assess the feasibility of using the proposed technology to acquire high quality EEG data and functional imaging, concurrent TMS/EEG/fMRI experiment was conducted using a phantom. To produce synthetic EEG data, the phantom's head was covered with a cloth immersed in a 9% NaCl solution with the 2-channel "RF-EEG Cap" placed above it. The cloth was connected to a signal generator outside the scanner that delivered a 5.1 Hz square signal at 20 mVpp (see FIG. 3B). TMS pulses were delivered as indicated by the dots in the TMS "ON" block shown in the time series of FIG. 6B, at 50% maximum stimulation output (MSO). Functional imaging (SL=3 mm, TR=1000 ms, TE=37 ms, FA=90°, 6 slices, 2.4 mm×2.4 mm in-plane) was interleaved with the TMS pulses that were delivered just before the acquisition of the $5^{th}$ slice (650 ms after volume starts). EEG data was recorded using the BrainAmp ExG MR 16 (Brain Products GmbH, Germany) and processed using EEGLab software package.

Results

Figure 4:
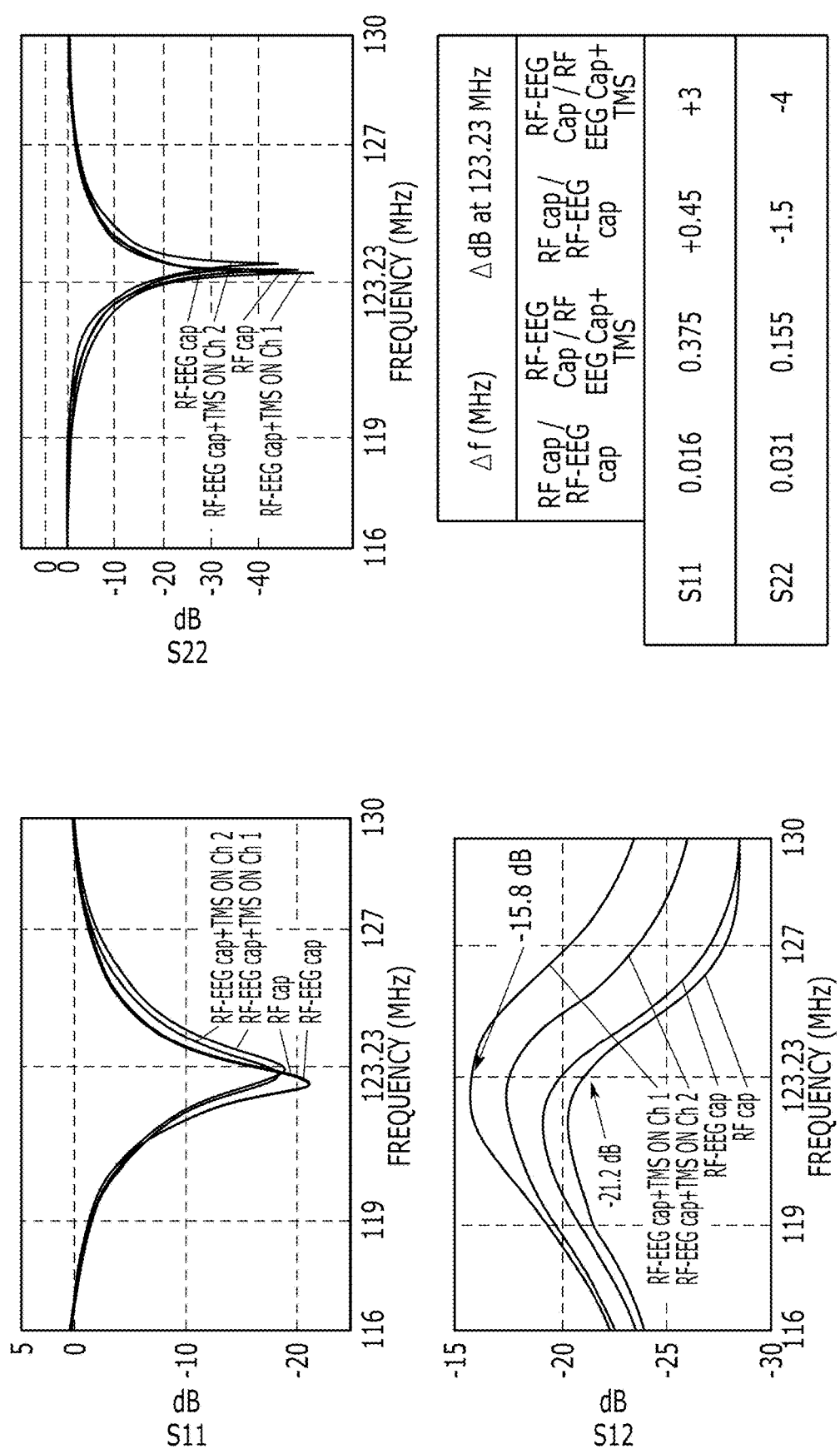
FIG. 4 shows a set of correlated experimental results demonstrating the effect of EEG leads and integration of a TMS coil on S-parameters of an RF cap.

The $Q_u/Q_l$ of the RF coil elements were 2.24 and 2.19. Bench test results for each condition are shown in FIG. 4, including a summary of the main effects on the S-parameters. The S-parameters, which represent the linear characteristics of RF coils, are shown with and without the integration of the EEG cap and TMS coil.

Figure 5A:
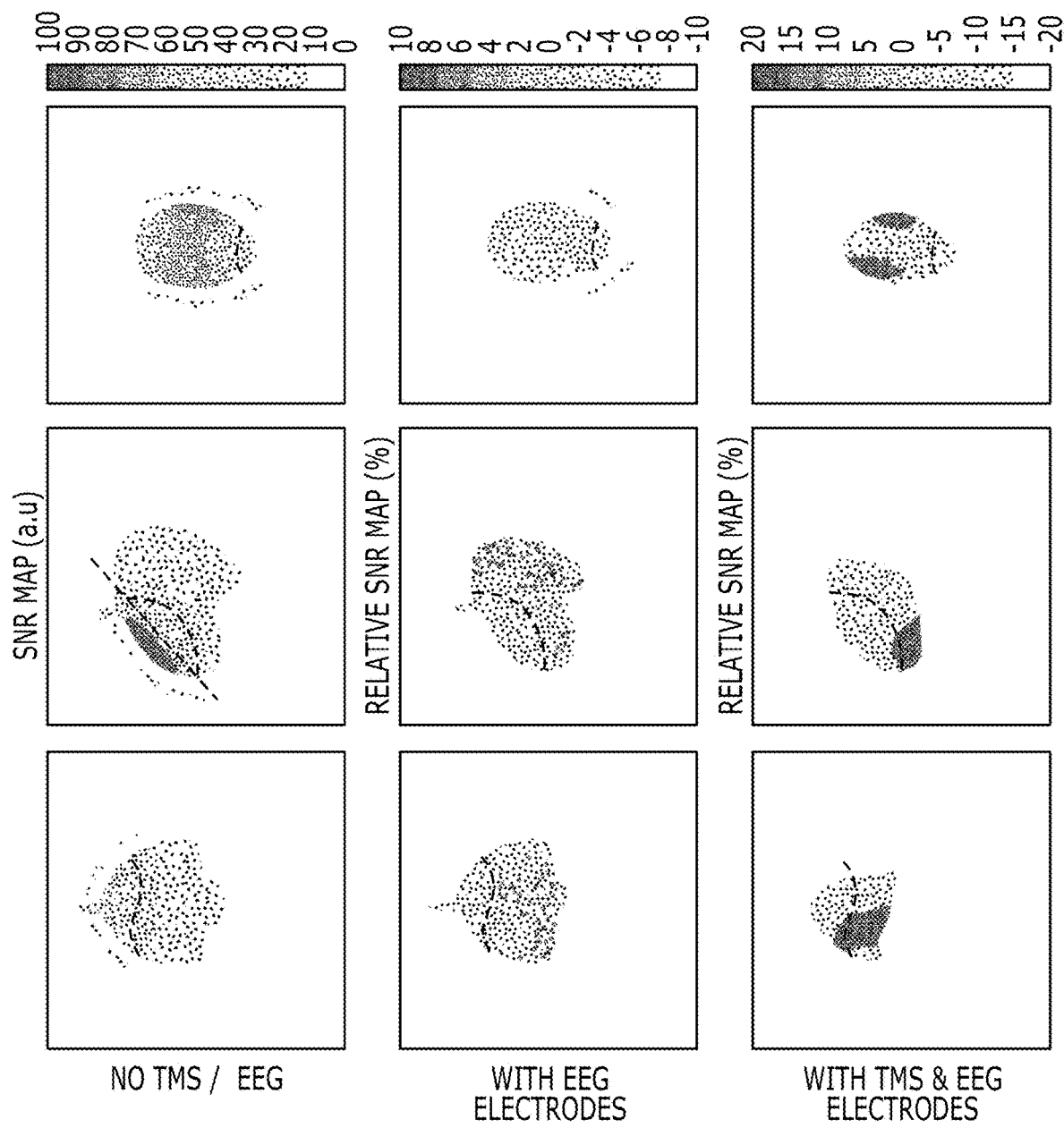
FIG. 5A shows experimental results demonstrating the effect of EEG leads and a TMS coil on signal to noise ratio (SNR).
Figure 5B:
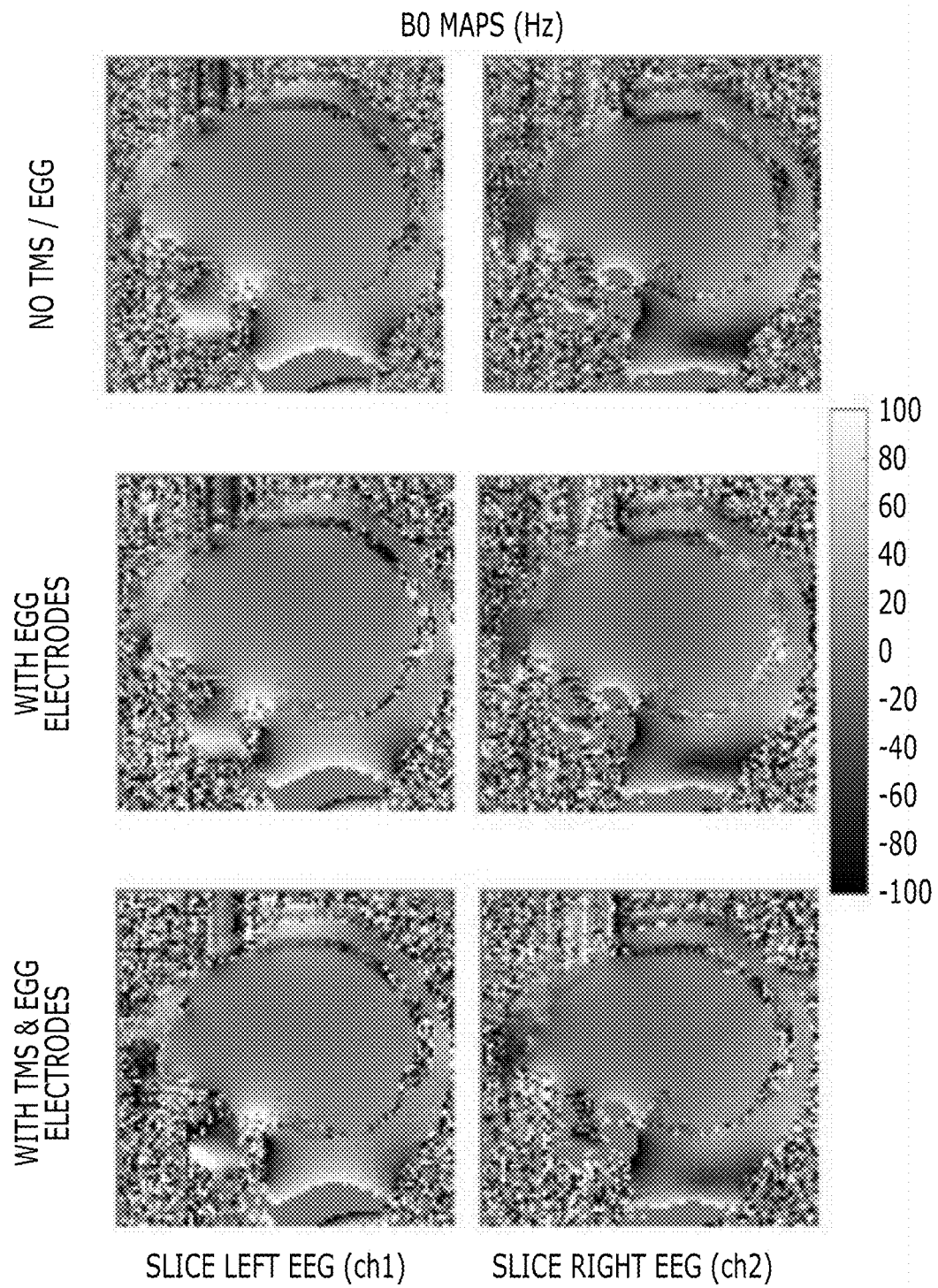
FIG. 5B shows experimental results demonstrating the effect of EEG leads and a TMS coil on $B_0$ homogeneity.

SNR maps of the 2-channel RF-EEG cap as stand-alone, without EEG-electrodes and TMS, is shown in the top row of FIG. 5A. The relative SNR for the case when the EEG-electrodes are included is shown in the middle row of FIG. 5A, and further adding the TMS coil placed over the left hemisphere of the phantom in the bottom row of FIG. 5A. When the EEG-electrodes are placed, no significant SNR change was observed over the region with sufficient SNR. In contrast, when the TMS coil was placed over the phantom, the well-known characterized B1 effect of TMS can be observed. No additional SNR changes are expected due to the presented technology. Sagittal $B_0$ maps directly over the EEG-electrodes are shown in FIG. 5B. No significant effects on the phantom brain due to the EEG-electrodes are visible.

Figure 6A:
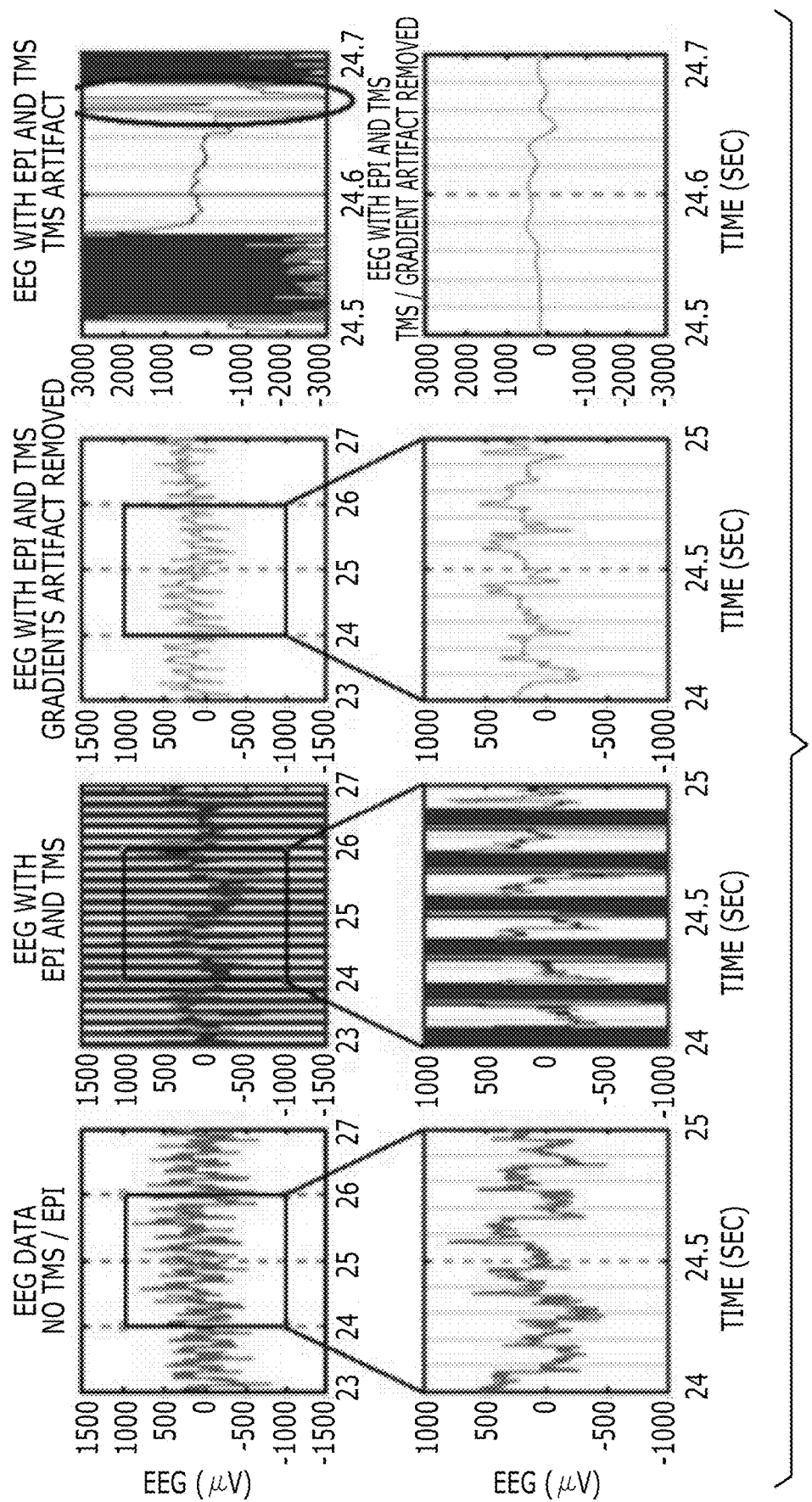
FIG. 6A shows a set of correlated experimental results demonstrating the quality of EEG data with and without simultaneous MRI acquisition and TMS for an experimental phantom setup as shown in FIG. 3B.
Figure 6B:
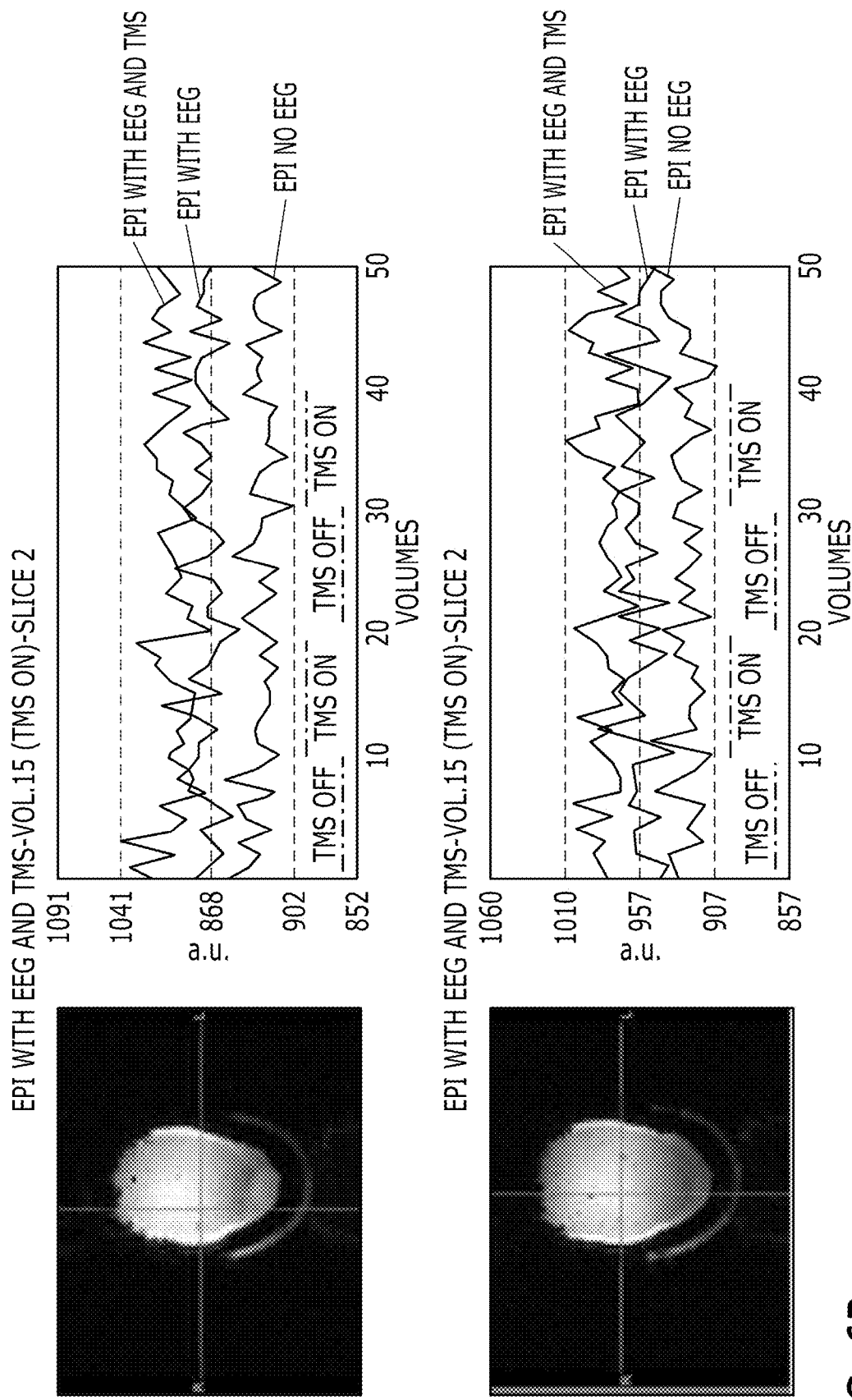
FIG. 6B shows a set of correlated experimental results demonstrating the quality of MRI images in the presence of EEG leads and TMS for an experimental phantom setup as shown in FIG. 3B.

The results of the quality analysis of the acquired EEG and fMRI data are presented in FIG. 6A and FIG. 6B, respectively. The TMS pulses and EEG acquisition did not affect the fMRI image quality as shown in the time series. FIG. 6A shows an analysis of EEG data quality. The first column shows the acquired synthetic EEG data from the phantom in the bore when no MR imaging was performed. The second column shows acquired synthetic EEG data from the phantom in the bore when MR imaging and TMS stimulation were performed in an interleaved way. The plots show all artifacts contaminating the EEG signal. The third column shows acquired synthetic EEG data acquired after removing gradient and TMS artifacts. The fourth column shows a more detailed view of the TMS artifact and how it was removed by post-processing.

FIG. 6B shows an analysis of echo planar imaging MRI with and without simultaneous EEG and TMS. The images show an EPI image during a TMS "on" period. The plots show the signal magnitude over a time series of alternating TMS with and without the presence of EEG acquisition.

Discussion

From the findings presented above it can be seen that the flexible coaxial RF technology is a feasible choice to build the proposed RF-EEG cap. The shifting effect on the resonance when placing the TMS over them was reported to be less than 0.4 MHz compared to 4-5 MHz when using standard copper wire coils. The minimal effects observed on the SNR, $B_0$ maps, EEG quality signal, and fMRI volumes and timeseries justify the further development of the RF-EEG cap to enable high quality data acquisition for concurrent TMS/EEG/fMRI experiments.

Example 2—Validate the Performance of the RF-EEG Cap System for Closed Loop TMS/fMRI/EEG Experiments The overarching goal is to obtain standard performance metrics for both imaging and electrophysiological data acquisition using the RF-EEG cap in humans. To validate the performance of each modality in vivo (EEG and fMRI), concurrent TMS/fMRI/EEG experiments may be performed on ten right-handed healthy volunteers. Repetitive TMS over left M1 (hand knob) can be applied with concurrent EEG and fMRI data acquisition while monitoring the TMS-elicited motor evoked potentials (MEPs) on the right first dorsal interosseous (FDI) using an MR compatible Electromyograph (EMG) to assure that pulses are consistently delivered to the target location with the intended intensity.

For example, in a first session, anatomical images can be acquired along with an M1 functional localizer using a finger tapping paradigm using the 32-channel standard head coil (Siemens, Erlangen). In a second session, the anatomical images and the functional localizer can be used for the MR compatible neuronavigation system to place the TMS over M1 of the subject's head with the integrated RF-EEG cap to acquire each subject's resting (RMT) and active (AMT) motor thresholds and then perform the experimental conditions in the scanner. Each subject can perform three consecutive experimental conditions randomized between subjects, for example: (i) rTMS at 3.125 Hz and 110% of individual RMT; (ii) rTMS at 3.125 Hz and 90% of individualized AMT and (iii) voluntary finger movements requiring dorsi-flexion of the right index finger. Finger movements can be triggered by visual stimuli in the scanner. The stimulation blocks can consist of 30 pulses, lasting about 10 s, followed by a baseline period of 25 s. In eight stimulation blocks in total, each subject may receive no more than 800 effective TMS pulses per day and half of them at subthreshold intensity, which follows the recommended safety guidelines.

fMRI may be collected using a 3 T Siemens Skyra (Siemens, Erlangen) scanner and the EEG data using an MR compatible amplifier (Brain Products Brain Amp Plus, Gilching). From the EEG data, cortically constrained minimum-norm estimate (MNE) linear inverse solution and dynamical statistical parametric maps (dSPM) may be calculated using an MEG/EEG analysis stream that is fully compatible with TMS-EEG data. The obtained results can be compared to previous publications using similar acquisition parameters. For the fMRI acquisitions, due to the expected high sensitivity of the novel instrumentation, functional images may be acquired with higher spatial and time resolution using fast fMRI techniques (for example, SMS-EPI 2.0 mm isotropic resolution, TE 31.0 ms, TR 663 ms, SMS=6) than in previous studies. Data may be evaluated using SPM to produce activation maps for individual and group results.

Results may be carefully compared with previous studies. Information about the TMS position during the experiments may be recorded by the neuronavigation system, which can account for higher reliability and control of the experiment. Additionally, EEG data can be stored as a repository to develop and validate a real-time algorithm for detecting defined phases on brain oscillations.

Example 3—Implement and Test the Closed Loop System for TMS

Standard algorithms may be used to remove gradient artifacts, TMS artifacts, and other MR environment related artifacts, to clean the acquired EEG data. Synchronization of the signal processing unit with the MR scanner clock and TMS can allow for closed loop experiments and artifact removal.

The instantaneous phase of brain oscillations is a key feature of regional neuronal processing. This information, when taken as an indicator of brain excitability, can be used to inform the timing of the TMS application to maximize the effects. Several existing methods for robust real-time EEG phase extraction may be used in closed loop TMS-EEG experiments. For example, an educated temporal prediction (ETP) algorithm may be used, which incorporates a training phase for the algorithm before the real-time application. Baseline EEG data may be acquired beforehand. Synthetic EEG data or human resting state EEG data from repositories may be used to test and validate the implemented algorithm.

The signal processing unit may be tested outside of the scanner, using EEG data to produce triggers when the target phase condition of the selected oscillation is present. The phase deviation between the signal phase when the trigger event is produced and the actual target phase may be reported. The signal processing unit may be further tested while processing the EEG data acquired using the RF-EEG cap on a phantom or subject in the scanner during a fMRI session in real-time. To generate realistic phantom data, EEG waveforms from resting-state human measurement may be used to drive the electrodes attached to the saline cloth under the RF-EEG cap.

Motion correction algorithms may be used to account for motion of the RF-EEG cap. Since the RF coil elements move together with the head in this setup, there may be an advantage of using the integrated setup for small movements. The intensity of each voxel can remain constant as the RF coils move with the subject and parallel imaging strategies may have less ghosting due to the invariance of the coil sensitivity profiles throughout the scan. Strategies to constrain head movements may also be implemented. For example, a 3D-printed head holder may be used to support the subject's neck to minimize movements while leaving the scalp accessible for stimulation.

Example 4—Closed Loop fMRI/EEG/TMS Experiment Using an RF-EEG Cap and Brain Mapping System A concurrent TMS/fMRI/EEG closed loop experiment may be performed on twenty right-handed healthy volunteers to trigger a train of theta burst stimulation (TBS) (3 pulses at 50 Hz) over the dorsolateral prefrontal cortex (DLPFC). The trigger may be based on the negative EEG peak of instantaneous alpha oscillations or using a random alpha phase. Triggering TMS at the negative peak of endogenous alpha oscillations in the left DLPFC may result in differential modulation of cortical excitability as compared to a random synchronization as measured by EEG/fMRI.

Each subject may undergo two experimental sessions. In the first session, anatomical images may be acquired using a standard 32-channel head coil. Baseline EEG data may be acquired to inform a signal processing unit to trigger the TMS in subsequent experiments. In a second session, the anatomical images can be used by the neuronavigation system in order to place the TMS coil over the left DLPFC of each subject. The intensity of the TMS may be set to 80% AMT. TMS administration may be synchronized either (i) at the negative EEG peak of instantaneous alpha oscillations or at (ii) random alpha phase control condition.

Functional images may be collected using a 3 T Siemens Skyra MRI scanner and EEG data may be collected using an MR compatible EEG amplifier. The signal processing pipeline described above may be used for the EEG and functional images. The acquired fMRI data may also be used to calculate functional connectivity (fc-MRI) to quantify the neuromodulatory effects on the typically targeted brain circuits for the treatment of MDD depending on the triggering condition. The subject and TMS coil position may be monitored using the MR compatible TMS neuronavigation system during the whole experiment in the scanner to ensure consistent delivery of the stimuli.

The TMS administration may be performed during pauses between consecutive EPI volume acquisitions. However, due to the nature of the closed loop system, it may not be ideal to limit the TMS pulses to the short pre-defined 'time slots' between volumes. Instead, timing information from the MRI scanner for each EPI slice may be used to determine when stimulation can be delivered, resulting in shorter delays until a "free time slot" when imaging gradients are "off" is reached to trigger TMS.

The system can provide next-generation brain mapping tools capable of performing causal brain mapping combining TMS/fMRI/EEG.

Figure 7:
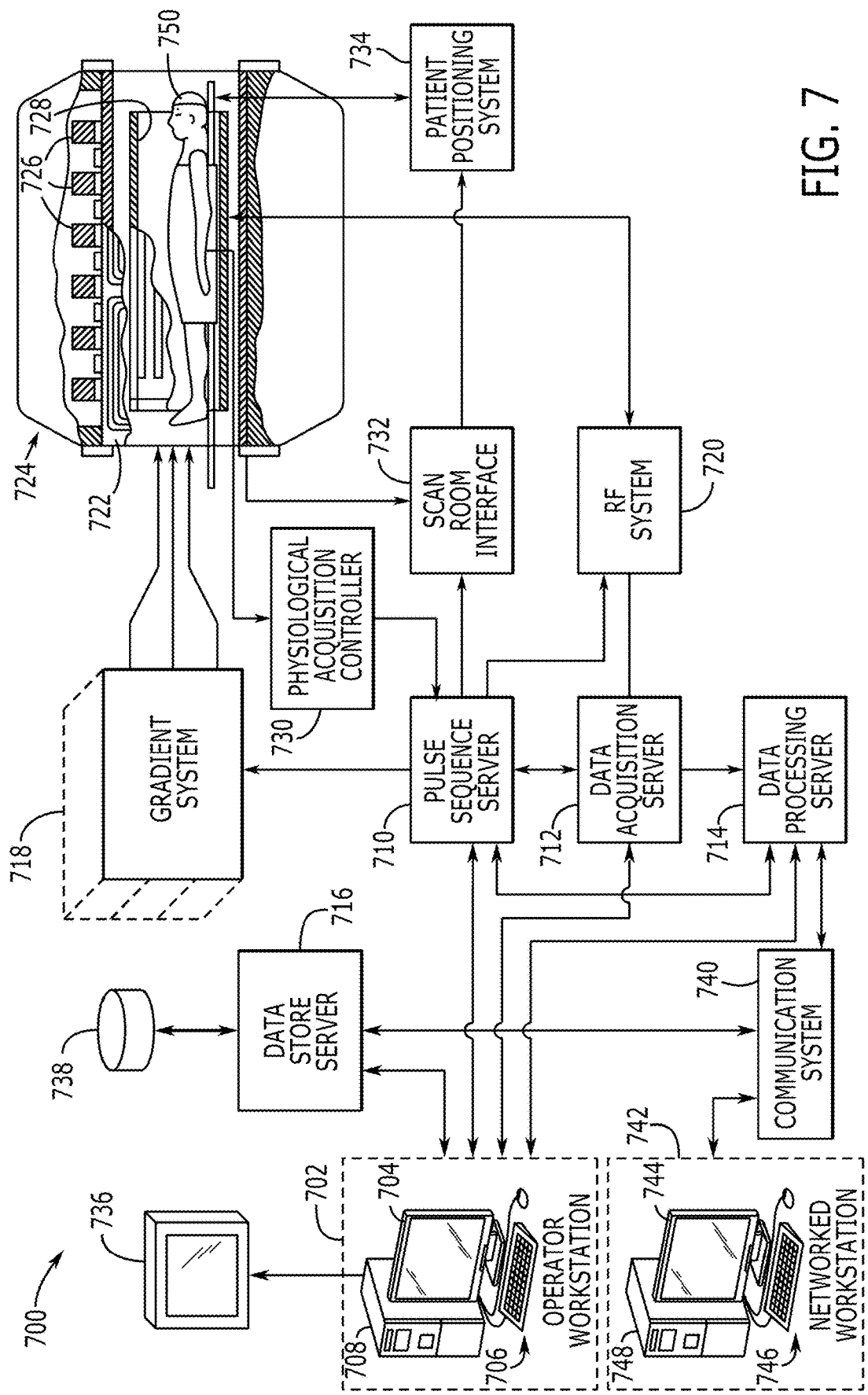
FIG. 7 is a block diagram of an example magnetic resonance imaging ("MRI") system that can implement the methods described in the present disclosure.

Referring particularly now to FIG. 7, an example of an MRI system 700 that can implement the methods described herein is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The MRI system 700 also includes a magnet assembly 724 that includes a polarizing magnet 726, which may be a low-field magnet. The MRI system 700 may optionally include a whole-body RF coil 728 and a gradient system 718 that controls a gradient coil assembly 722. The MRI system 700 may also include an RF cap 750 as part of an RF-EEG cap, according to some aspects of the present disclosure.

The pulse sequence server 710 functions in response to instructions provided by the operator workstation 702 to operate a gradient system 718 and a radiofrequency ("RF") system 720. Gradient waveforms for performing a prescribed scan are produced and applied to the gradient system 718, which then excited gradient coils in an assembly 722 to produce the magnetic field gradients (e.g., $G_x$, $G_y$, and $G_z$) that can be used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the magnetic resonance signal. In a non-limiting example, a birdcage receive coil may be used while driven in quadrature, in which the I and Q quadrature components of the magnetic resonance signal are received and digitized. The magnitude of the received magnetic resonance signal may, therefore, be determined at a sampled point by the square root of the sum of the squares of the I and Q components:

$$M=\sqrt{(I^2+Q^2)}.$$

and the phase of the received magnetic resonance signal may also be determined according to the following relationship:

$$\phi = \tan^{-1}\left(\frac{Q}{I}\right)$$

Surface array coils may also be used as part of the RF system 720, in which parallel imaging or other techniques may be used to combine the signals from individual channels.

The pulse sequence server 710 may receive patient data from a physiological acquisition controller 730. By way of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heartbeat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data are not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

Figure 8:
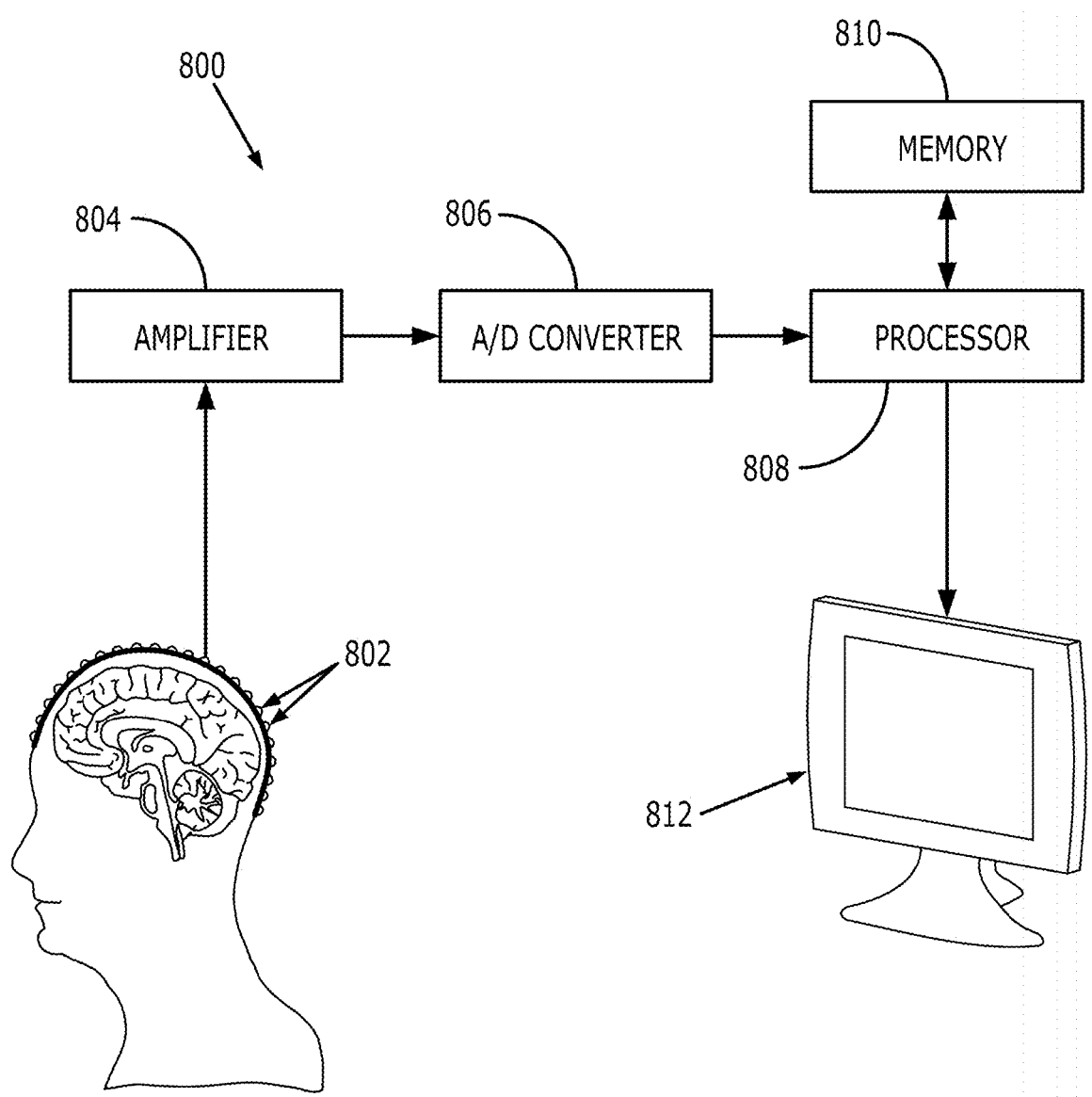
FIG. 8 is a block diagram of an exemplary electroencephalography system in accordance with some aspects of the present disclosure.

Referring now to FIG. 8, an exemplary electroencephalography ("EEG") system 800 for acquiring electrophysiological signals indicative of neuronal activity is illustrated. The electrophysiological signals measured and acquired with the EEG system 800 are acquired on a number of EEG electrodes 802, or sensors, for example, of the 10-20 international electrode placement system.

During measurement of neuronal activity with the EEG system, a continuous stream of voltage data representative of an electrophysiological signal is detected by the electrodes 802, which are coupled to the subject's scalp, and the acquired signals are sampled and digitized. Specifically, an amplifier 804 in communication with the electrodes 802 is used to amplify the acquired signals, after which the amplified signals are sent to an analog-to-digital ("A/D") converter 806 that converts the signals from analog to digital format. The acquired signals can also undergo additional preprocessing in order to remove artifacts, such as those due to data collection and physiological causes. The digital signals are sent to a processor 808 that processes the signals as described in detail above. The processor 808 is also configured to store the processed or unprocessed signals in a memory 810, and to display the signals on a display 812.

Figure 9B:
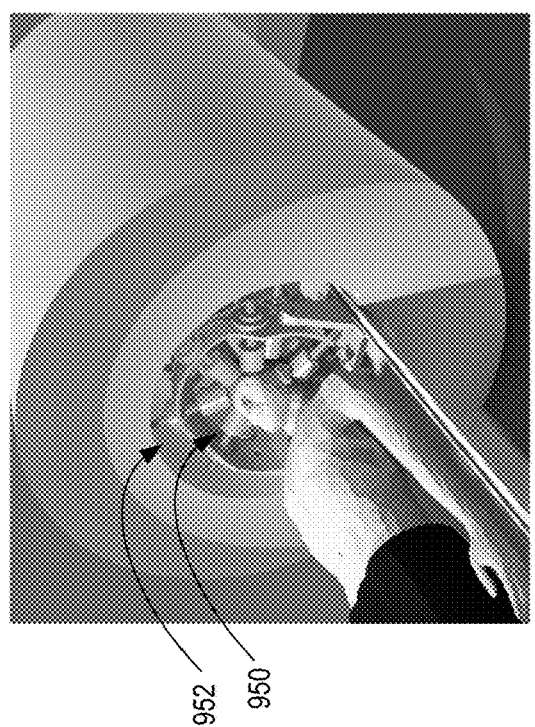
FIG. 9B illustrates an example of a TMS system that includes a multichannel coil array in accordance with some aspects of the present disclosure.
Figure 9A:
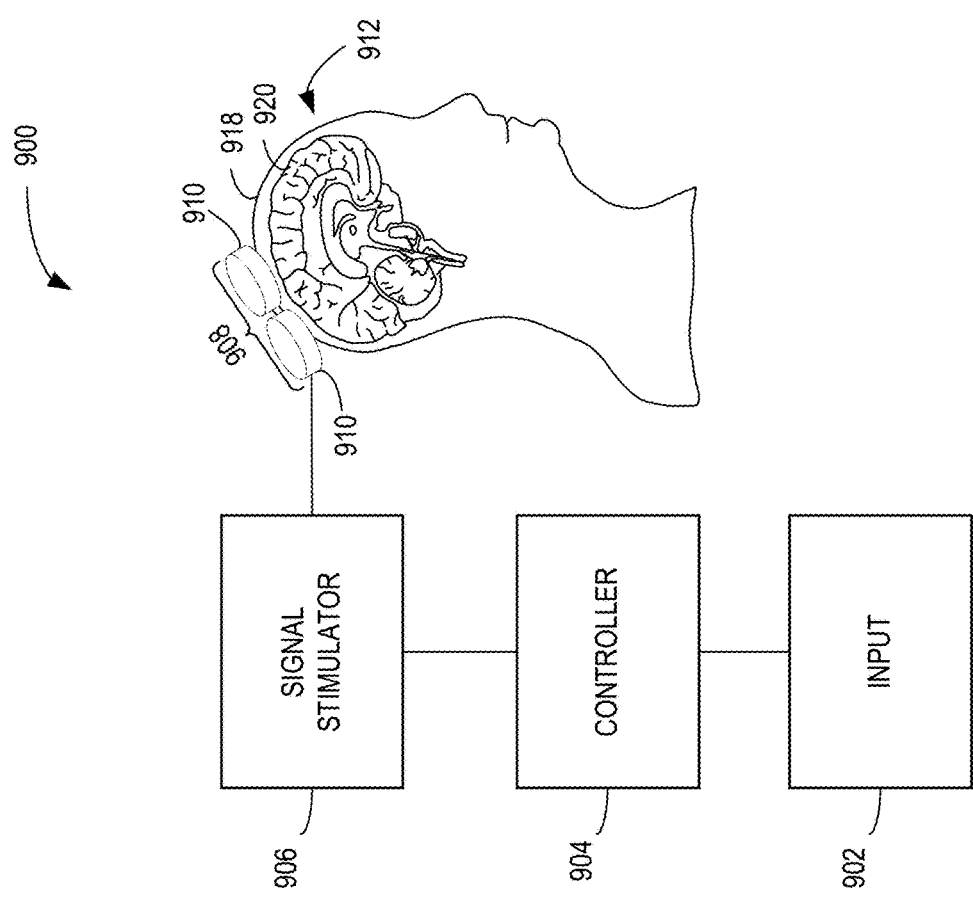
FIG. 9A is a block diagram of an example transcranial magnetic stimulation (TMS) system in accordance with some aspects of the present disclosure.

FIG. 9A is a block diagram of an example transcranial magnetic stimulation (TMS) system in accordance with some aspects of the present disclosure. The TMS system 900 may include an input 902, a controller 904, and an electromagnetic coil array 908. The TMS system 900 may also include a signal source that may be a signal stimulator 906. For example, the signal stimulator 906 may include a high voltage capacitor that is capable of producing a high changing current when a switch is activated, connecting the inductor L to the high voltage charged capacitor, for example. The TMS system 900 may include one or more TMS coils 910 arranged in a TMS coil array 908. The TMS coils 910 may be high inductance coils that can discharge the high voltage from the signal stimulator 906 as a changing current through the coils 910, which induces a magnetic field.

The controller 904 is in communication with the signal stimulator 906 and is configured to direct the signal stimulator 906 to provide various signals to the coil array 908. In some implementations, the controller 904 may be any general-purpose computing system or device, such as a personal computer, workstation, cellular phone, smartphone, laptop, tablet, or the like. As such, the controller 904 may include any suitable hardware and components designed or capable of carrying out a variety of processing and control tasks, including steps for optimizing and directing the signal stimulator 906 to provide various signals to the coil array 908. For example, the controller 904 may include a programmable processor or combination of programmable processors, such as central processing units (CPUs), graphics processing units (GPUs), and the like. In some implementations, the controller 904 may be configured to execute instructions stored in a non-transitory computer readable-media. In this regard, the controller 904 may be any device or system designed to integrate a variety of software, hardware, capabilities and functionalities. Alternatively, and by way of particular configurations and programming, the controller 904 may be a special-purpose system or device. For instance, such special-purpose system or device may include one or more dedicated processing units or modules that may be configured (e.g., hardwired, or pre-programmed) to carry out steps, in accordance with aspects of the present disclosure.

The electromagnetic coil array 908 is positioned proximate to and over the head, for example, the scalp 918, of a subject 912. The placement of the TMS coil array 908 may be informed by MRI or EEG data as previously described. The electromagnetic coil array 908 may be insulated using known methods and materials. In some aspects, the coil array 908 may be positioned and held in place over the scalp 918 by an operator or using a mechanical arm (not shown). The position of the coil array 908 over the scalp 918 is selected to target and stimulate a specific area of the brain (e.g., a region, site or target in the brain). Accordingly, the coil array 908 may be positioned over the region to be stimulated in the brain. The signal stimulator 906 is configured to generate and deliver electrical signals (e.g., electric current) to the coil array 908. The electric current delivered from the signal stimulator 906 and flowing through the coil array 908 generates a magnetic field. The magnetic field (e.g., magnetic pulses) passes through the skull and into the brain 920 of the subject 912 and cause or induce electrical currents that stimulate nerve cells in the targeted brain region. Different coil types may be used for coil array 908 to elicit different magnetic field patterns. The strength and distribution of the time-varying magnetic fields may be dependent on both the geometry and the amount of current traveling through the coil array 908. The induced electric field may also be dependent on fixed variables unique to individual subjects such as the geometry and electrical properties of anatomies in and around the brain. The induced electric field may also be triggered by the user or by the controller 1104 based on external data, such as MRI data, fMRI data, EEG data, or the like.

In some aspects, the signals or electrical current pulses, which are generated by the signal stimulator 906 and provided to the coil array 908, may be in the form of a pulse sequence having a plurality of pulses. The power, amplitude, duration, shape, and frequency of the pulses may be selected to achieve a desired level of or depth of stimulation, as well as to optimize heat or magnetic forces induced in the coil array 908. An operator may select the specific type and characteristics of the electric pulses to be generated by the signal stimulator 906 using an input 902 coupled to the controller 904. The input 902 can be, for example, a keyboard, a mouse, a touch screen, or the like. While the following description will be discussed in referenced to a TMS system and a TMS coil, it should be understood that the systems and methods described herein may be used with other types of non-invasive neuromodulation systems.

Referring now to FIG. 9B, an example of a multi-channel TMS coil array 950 is shown, which may be used in a bore 952 of an MRI system as described throughout the present disclosure. The TMS coil array 950 may include multiple TMS coils that are arranged in an array. For example, the TMS coil array 950 may include as few as two coils but may include many more, such as 20, 40 or even more. The number of TMS coils within the TMS coil array may be determined based, at least in part, on the size of each TMS coil, the size of the head of the patient, or the amount of space available in the MRI bore 952, for example. The individual TMS coils may be equally spaced around the scalp of the patient or may be spaced in another arrangement suitable for localized stimulation. The arrangement of TMS coils within the TMS coil array 950 may be fixed, in which the stimulation localization can be controlled by selectively stimulating one or more coils located near the desired brain region. The arrangement of TMS coils within the TMS coil array 950 may also be variable in which the placement of each coil within the TMS coil array 950 may be determined based in part on the location of the target stimulation region or another constraint, such as available bore space.

Figure 10:
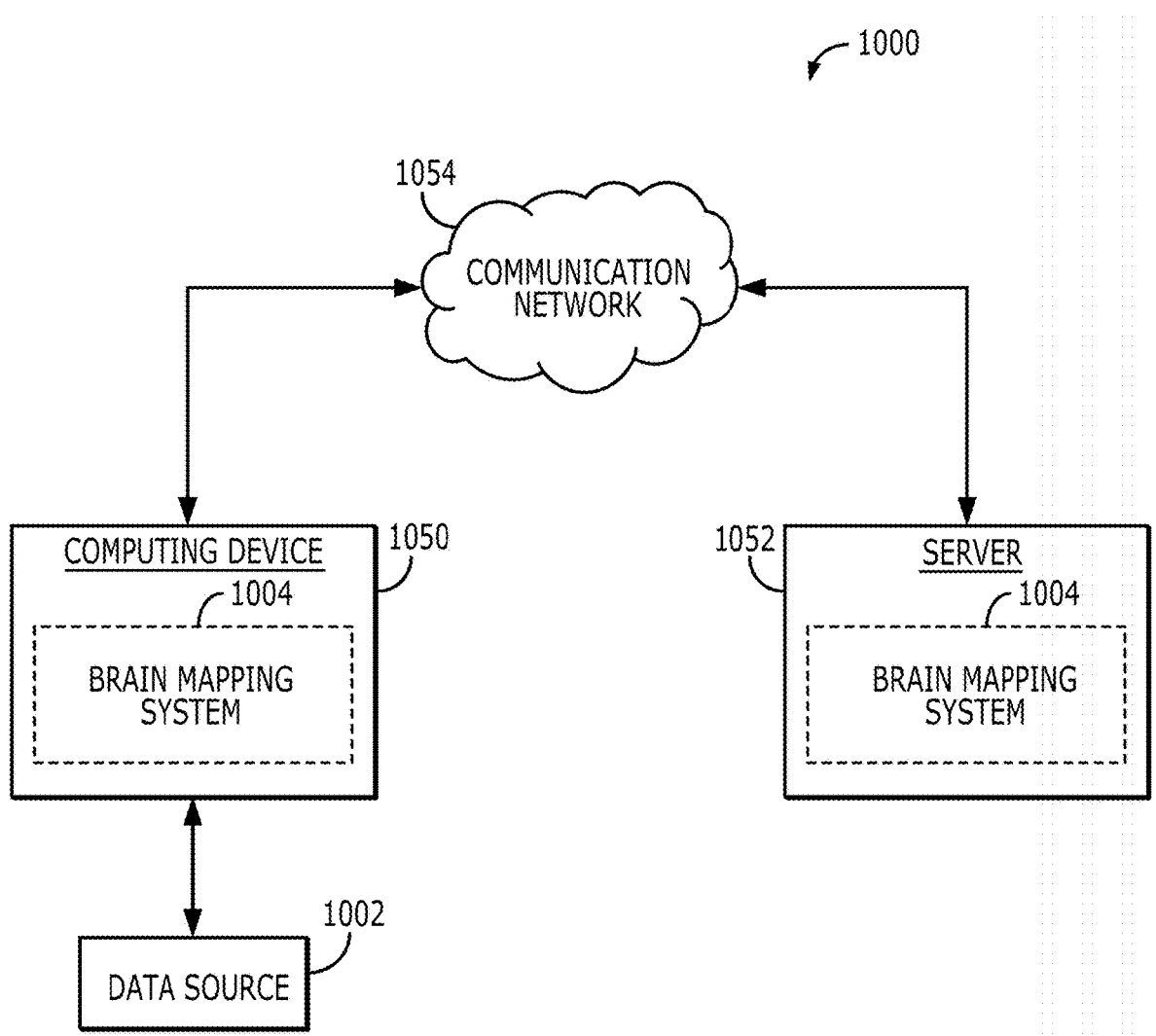
FIG. 10 is a block diagram of an example brain mapping system that can implement the methods of the present disclosure.

Referring now to FIG. 10, an example of an MRI system 1000 is shown, which may be used in accordance with some aspects of the systems and methods described in the present disclosure. As shown in FIG. 10, a computing device 1050 can receive one or more types of data (e.g., signal evolution data, k-space data, receiver coil sensitivity data, EEG data, TMS data, or the like) from data source 1002. In some configurations, computing device 1050 can execute at least a portion of a brain mapping system 1004 to reconstruct images from magnetic resonance data (e.g., k-space data) acquired using a standard MRI or fMRI technique. In some configurations, the brain mapping system 1004 can implement an automated pipeline to provide MRI images, fMRI data, or the like. The brain mapping system 1004 may also receive and analyze EEG data. The brain mapping system 1004 may use MRI data, EEG data, or a combination thereof to determine a placement of a TMS coil or a trigger time for applying TMS.

Additionally or alternatively, in some configurations, the computing device 1050 can communicate information about data received from the data source 1002 to a server 1052 over a communication network 1054, which can execute at least a portion of the brain mapping system 1004. In such configurations, the server 1052 can return information to the computing device 1050 (and/or any other suitable computing device) indicative of an output of the brain mapping system 1004.

In some configurations, computing device 1050 and/or server 1052 can be any suitable computing device or combination of devices, such as a desktop computer, a laptop computer, a smartphone, a tablet computer, a wearable computer, a server computer, a virtual machine being executed by a physical computing device, and so on. The computing device 1050 and/or server 1052 can also reconstruct images from the data.

In some configurations, data source 1002 can be any suitable source of data (e.g., measurement data, images reconstructed from measurement data, processed image data, EEG time course data, TMS status data, TMS plan data, or the like), such as an MRI system, an EEG system, a TMS system, a neuronavigation system, another computing device (e.g., a server storing measurement data, images reconstructed from measurement data, processed image data, processed EEG data), and so on. In some configurations, data source 1002 can be local to computing device 1050. For example, data source 1002 can be incorporated with computing device 1050 (e.g., computing device 1050 can be configured as part of a device for measuring, recording, estimating, acquiring, or otherwise collecting or storing data). As another example, data source 1002 can be connected to computing device 1050 by a cable, a direct wireless link, and so on. Additionally or alternatively, in some configurations, data source 1002 can be located locally and/or remotely from computing device 1050, and can communicate data to computing device 1050 (and/or server 1052) via a communication network (e.g., communication network 1054).

In some configurations, communication network 1054 can be any suitable communication network or combination of communication networks. For example, communication network 1054 can include a Wi-Fi network (which can include one or more wireless routers, one or more switches, or the like), a peer-to-peer network (e.g., a Bluetooth network), a cellular network (e.g., a 3G network, a 4G network, or the like, complying with any suitable standard, such as CDMA, GSM, LTE, LTE Advanced, WiMAX, or the like), other types of wireless network, a wired network, and so on. In some configurations, communication network 1054 can be a local area network, a wide area network, a public network (e.g., the Internet), a private or semi-private network (e.g., a corporate or university intranet), any other suitable type of network, or any suitable combination of networks. Communications links shown in FIG. 10 can each be any suitable communications link or combination of communications links, such as wired links, fiber optic links, Wi-Fi links, Bluetooth links, cellular links, and so on.

Figure 11:
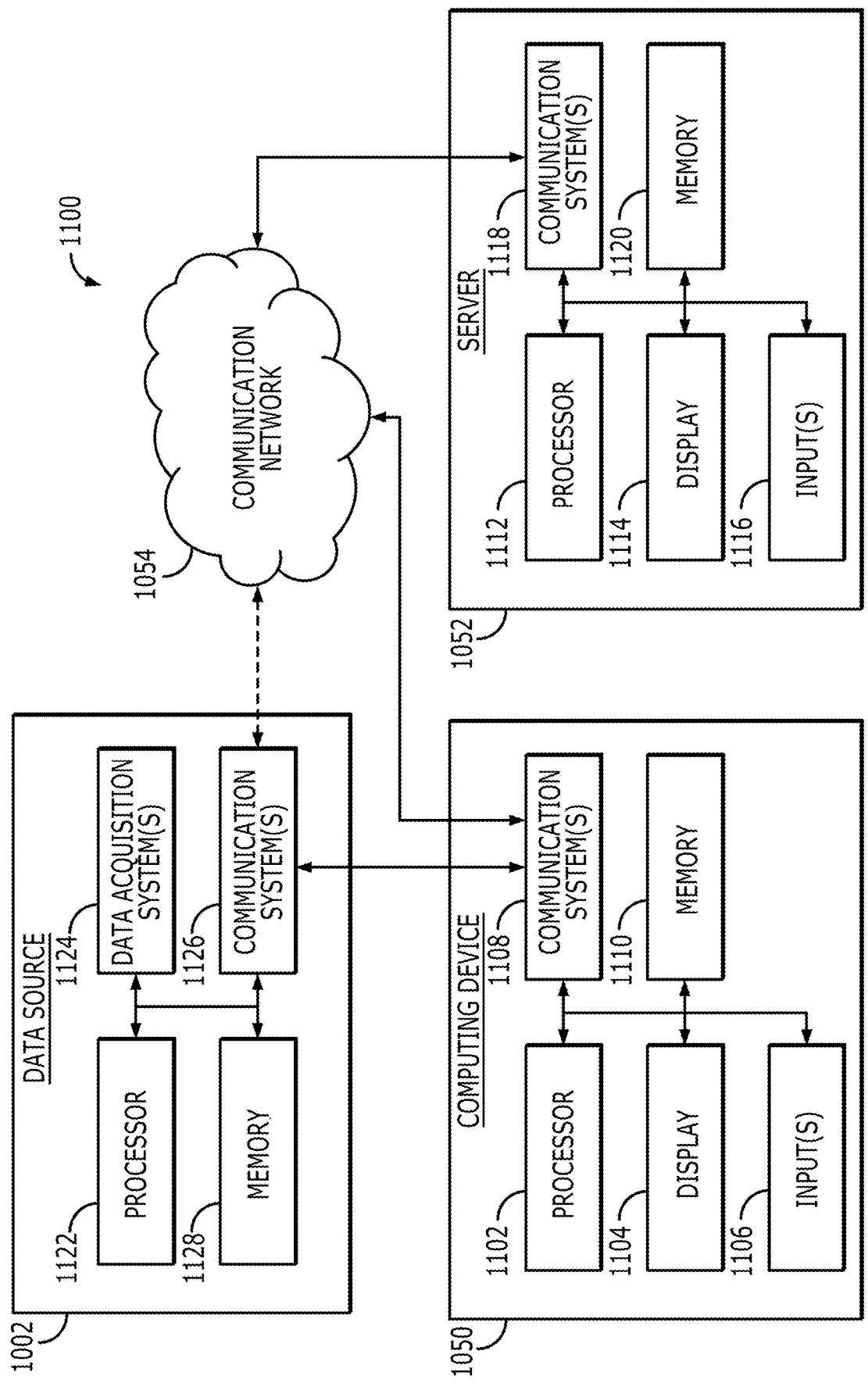
FIG. 11 is a block diagram of example components that can implement the system of FIG. 10.

Referring now to FIG. 11, an example of hardware 1100 that can be used to implement data source 1002, computing device 1050, and server 1052 in accordance with some configurations of the systems and methods described in the present disclosure is shown.

As shown in FIG. 11, in some configurations, computing device 1050 can include a processor 1102, a display 1104, one or more inputs 1106, one or more communication systems 1108, and/or memory 1110. In some configurations, processor 1102 can be any suitable hardware processor or combination of processors, such as a central processing unit ("CPU"), a graphics processing unit ("GPU"), and so on. In some configurations, display 1104 can include any suitable display devices, such as a liquid crystal display ("LCD") screen, a light-emitting diode ("LED") display, an organic LED ("OLED") display, an electrophoretic display (e.g., an "e-ink" display), a computer monitor, a touchscreen, a television, and so on. In some configurations, inputs 1106 can include any suitable input devices and/or sensors that can be used to receive user input, such as a keyboard, a mouse, a touchscreen, a microphone, and so on.

In some configurations, communications systems 1108 can include any suitable hardware, firmware, and/or software for communicating information over communication network 1054 and/or any other suitable communication networks. For example, communications systems 1108 can include one or more transceivers, one or more communication chips and/or chip sets, and so on. In a more particular example, communications systems 1108 can include hardware, firmware, and/or software that can be used to establish a Wi-Fi connection, a Bluetooth connection, a cellular connection, an Ethernet connection, and so on.

In some configurations, memory 1110 can include any suitable storage device or devices that can be used to store instructions, values, data, or the like, that can be used, for example, by processor 1102 to present content using display 1104, to communicate with server 1052 via communications system(s) 1108, and so on. Memory 1110 can include any suitable volatile memory, non-volatile memory, storage, or any suitable combination thereof. For example, memory 1110 can include random-access memory ("RAM"), read-only memory ("ROM"), electrically programmable ROM ("EPROM"), electrically erasable ROM ("EEPROM"), other forms of volatile memory, other forms of non-volatile memory, one or more forms of semi-volatile memory, one or more flash drives, one or more hard disks, one or more solid state drives, one or more optical drives, and so on. In some configurations, memory 1110 can have encoded thereon, or otherwise stored therein, a computer program for controlling operation of computing device 1050. In such configurations, processor 1102 can execute at least a portion of the computer program to present content (e.g., images, user interfaces, graphics, tables), receive content from server 1052, transmit information to server 1052, and so on. For example, the processor 1102 and the memory 1110 can be configured to perform the methods described herein.

In some configurations, server 1052 can include a processor 1112, a display 1114, one or more inputs 1116, one or more communications systems 1118, and/or memory 1120. In some configurations, processor 1112 can be any suitable hardware processor or combination of processors, such as a CPU, a GPU, and so on. In some configurations, display 1114 can include any suitable display devices, such as an LCD screen, LED display, OLED display, electrophoretic display, a computer monitor, a touchscreen, a television, and so on. In some configurations, inputs 1116 can include any suitable input devices and/or sensors that can be used to receive user input, such as a keyboard, a mouse, a touchscreen, a microphone, and so on.

In some configurations, communications systems 1118 can include any suitable hardware, firmware, and/or software for communicating information over communication network 1054 and/or any other suitable communication networks. For example, communications systems 1118 can include one or more transceivers, one or more communication chips and/or chip sets, and so on. In a more particular example, communications systems 1118 can include hardware, firmware, and/or software that can be used to establish a Wi-Fi connection, a Bluetooth connection, a cellular connection, an Ethernet connection, and so on.

In some configurations, memory 1120 can include any suitable storage device or devices that can be used to store instructions, values, data, or the like, that can be used, for example, by processor 1112 to present content using display 1114, to communicate with one or more computing devices 1050, and so on. Memory 1120 can include any suitable volatile memory, non-volatile memory, storage, or any suitable combination thereof. For example, memory 1120 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some configurations, memory 1120 can have encoded thereon a server program for controlling operation of server 1052. In such configurations, processor 1112 can execute at least a portion of the server program to transmit information and/or content (e.g., data, images, a user interface) to one or more computing devices 1050, receive information and/or content from one or more computing devices 1050, receive instructions from one or more devices (e.g., a personal computer, a laptop computer, a tablet computer, a smartphone), and so on.

In some configurations, the server 1052 is configured to perform the methods described in the present disclosure. For example, the processor 1112 and memory 1120 can be configured to perform the methods described herein.

In some configurations, data source 1002 can include a processor 1122, one or more data acquisition systems 1124, one or more communications systems 1126, and/or memory 1128. In some configurations, processor 1122 can be any suitable hardware processor or combination of processors, such as a CPU, a GPU, and so on. In some configurations, the one or more data acquisition systems 1124 are generally configured to acquire data, images, or both, and can include an MRI system. Additionally or alternatively, in some configurations, the one or more data acquisition systems 1124 can include any suitable hardware, firmware, and/or software for coupling to and/or controlling operations of an MRI system. In some configurations, one or more portions of the data acquisition system(s) 1124 can be removable and/or replaceable.

Note that, although not shown, data source 1002 can include any suitable inputs and/or outputs. For example, data source 1002 can include input devices and/or sensors that can be used to receive user input, such as a keyboard, a mouse, a touchscreen, a microphone, a trackpad, a trackball, and so on. As another example, data source 1002 can include any suitable display devices, such as an LCD screen, an LED display, an OLED display, an electrophoretic display, a computer monitor, a touchscreen, a television, or the like, one or more speakers, and so on.

In some configurations, communications systems 1126 can include any suitable hardware, firmware, and/or software for communicating information to computing device 1050 (and, in some configurations, over communication network 1054 and/or any other suitable communication networks). For example, communications systems 1126 can include one or more transceivers, one or more communication chips and/or chip sets, and so on. In a more particular example, communications systems 1126 can include hardware, firmware, and/or software that can be used to establish a wired connection using any suitable port and/or communication standard (e.g., VGA, DVI video, USB, RS-232, or the like), Wi-Fi connection, a Bluetooth connection, a cellular connection, an Ethernet connection, and so on.

In some configurations, memory 1128 can include any suitable storage device or devices that can be used to store instructions, values, data, or the like, that can be used, for example, by processor 1122 to control the one or more data acquisition systems 1124, and/or receive data from the one or more data acquisition systems 1124; to generate images from data; present content (e.g., data, images, a user interface) using a display; communicate with one or more computing devices 1050; and so on. Memory 1128 can include any suitable volatile memory, non-volatile memory, storage, or any suitable combination thereof. For example, memory 1128 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some configurations, memory 1128 can have encoded thereon, or otherwise stored therein, a program for controlling operation of medical image data source 1002. In such configurations, processor 1122 can execute at least a portion of the program to generate images, transmit information and/or content (e.g., data, images, a user interface) to one or more computing devices 1050, receive information and/or content from one or more computing devices 1050, receive instructions from one or more devices (e.g., a personal computer, a laptop computer, a tablet computer, a smartphone, or the like), and so on.

In some configurations, any suitable computer-readable media can be used for storing instructions for performing the functions and/or processes described herein. For example, in some configurations, computer-readable media can be transitory or non-transitory. For example, non-transitory computer-readable media can include media such as magnetic media (e.g., hard disks, floppy disks), optical media (e.g., compact discs, digital video discs, Blu-ray discs), semiconductor media (e.g., RAM, flash memory, EPROM, EEPROM), any suitable media that is not fleeting or devoid of any semblance of permanence during transmission, and/or any suitable tangible media. As another example, transitory computer-readable media can include signals on networks, in wires, conductors, optical fibers, circuits, or any suitable media that is fleeting and devoid of any semblance of permanence during transmission, and/or any suitable intangible media.

Figure 12:
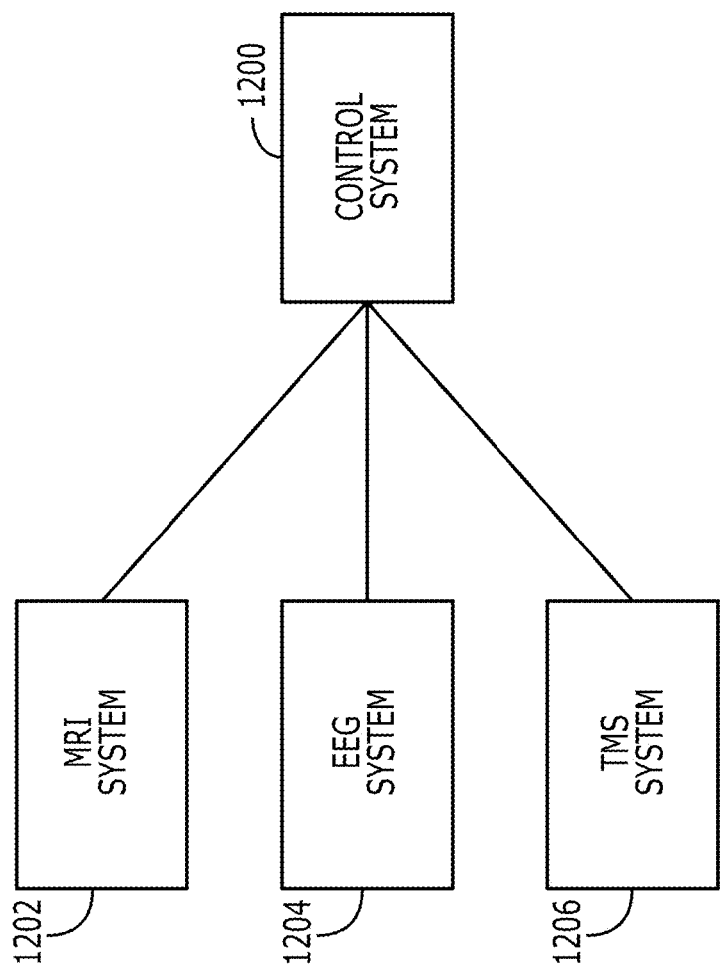
FIG. 12 is a block diagram of an example brain mapping system in accordance with some aspect of the present disclosure.

Referring now to FIG. 12, a block diagram is shown illustrating components of an example brain mapping system 1004 according to some aspects of the present disclosure. The brain mapping system 1004 may include a control system 1200 that can control an MRI system 1202, and EEG system 1204, and a TMS system 1206. The control system 1200 can be used to coordinate timing of the MRI acquisition by the MRI system 1202, EEG data acquisition by the EEG system 1204, and stimulation application by the TMS system 1206. The control system 1200 may also be used by the user to define parameters of the MRI system 1202, EEG system 1204, and TMS system 1206, as described above. The MRI system 1202 may include components as described with respect to FIG. 7, for example. The EEG system 1204 may be an MR-compatible system with MR-safe EEG electrodes. The EEG system 1204 may include components as described with respect to FIG. 8, for example. The TMS system 1206 may include components as described with respect to FIG. 9A, for example. The TMS system 1206 may further include a neuronavigation system. Other variations of the systems (i.e., 1202, 1204, 1206) may be used as well.

As used herein in the context of computer implementation, unless otherwise specified or limited, the terms "component," "system," "module," "controller," "framework," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present disclosure has described one or more preferred embodiments, and it should be appreciated that many equivalents, alternatives, variations, and modifications, aside from those expressly stated, are possible and within the scope of the invention.

The invention claimed is:

1. An integrated brain-mapping system for simultaneous magnetic resonance imaging (MRI) and electroencephalogram (EEG), wherein the system comprises:
   an integrated radiofrequency (RF)-EEG cap comprising:
      an EEG cap comprising a first layer of material containing a first plurality of holes that provide placeholders configured to receive EEG electrodes;
      an RF cap comprising a second layer of material containing a second plurality of holes and a plurality of RF coils fixed onto the second layer of material; and
      one or more fasteners configured to co-register the second plurality of holes to the first plurality of holes and to removably secure the RF cap to the EEG cap.

2. The integrated brain-mapping system of claim 1, further comprising a first plurality of grommets configured to line perimeters of the first plurality of holes and a second plurality of grommets configured to line perimeters of the second plurality of holes.

3. The integrated brain-mapping system of claim 1, wherein the one or more fasteners comprise a first plurality of grommets configured to line perimeters of the first plurality of holes and a second plurality of grommets configured to line perimeters of the second plurality of holes.

4. The integrated brain-mapping system of claim 1, wherein the one or more fasteners are snap fasteners.

5. The integrated brain-mapping system of claim 1, wherein the plurality of RF coils are loop coils comprising center regions and each of the second plurality of holes is positioned in a respective center region of a loop coil such that the respective loop coil does not overlap the respective hole.

6. The integrated brain-mapping system of claim 1, wherein the plurality of RF coils are loop coils comprising center regions;
   wherein each of the plurality of RF coils is positioned such that a part of the center region of a first loop coil overlaps with a part of the center region of a second loop coil to define an overlapping region; and wherein at least one hole of the second plurality of holes is positioned within the overlapping region.

7. The integrated brain-mapping system of claim 1, wherein the integrated RF-EEG cap further comprises a cover comprising a third layer of material removably fixed onto an outer surface of the RF cap to isolate the RF coils, wherein the third layer of material comprises a third plurality of holes configured to axially align with the second plurality of holes.

8. The integrated brain-mapping system of claim 7, wherein the third layer of material comprises medical synthetic leather to provide stability, component protection, and electrical insulation.

9. The integrated brain-mapping system of claim 1, wherein the integrated RF-EEG cap is modular such that the EEG cap and RF cap are configured to be functionally independent.

10. The integrated brain-mapping system of claim 1, further comprising an EEG electrical connection extending from the EEG cap to communicate EEG electrical signals received from a patient wearing the EEG cap and comprising an RF electrical connection extending from the RF cap to communicate at least one of transmit RF electrical signals to the RF cap or receive RF electrical signals received from a patient wearing the RF cap.

11. The integrated brain-mapping system of claim 10, wherein the EEG cap is configured to communicate the EEG electrical signals along the EEG electrical connection and the RF cap is configured to communicate the RF electrical signals along the RF electrical connection independently and operably, with or without the one or more fasteners co-registering the second plurality of holes to the first plurality of holes and securing the RF cap to the EEG cap.

12. The integrated brain-mapping system of claim 1, wherein the integrated RF-EEG cap is characterized by a total thickness that is greater than 0 mm and does not exceed 10 mm.

13. The integrated brain-mapping system of claim 1, wherein the integrated RF-EEG cap is fabricated to fit a head of a particular subject.

14. The integrated brain-mapping system of claim 1, wherein the system further comprises a plurality of EEG electrodes positioned in the placeholders.

15. The integrated brain-mapping system of claim 1, wherein an electric field of the plurality of RF coils is characterized;

wherein the system further comprises a plurality of cables, wherein each of the plurality of cables connects a respective EEG electrode to an EEG amplifier; and wherein each of the plurality of cables is routed through a path of minimum electric field based on the characterized electric field.

16. The integrated brain-mapping system of claim 1, wherein the system further comprises an external transcranial magnetic stimulation (TMS) coil configured to produce a magnetic field, wherein the TMS coil is positioned outside the integrated RF-EEG cap over a head of a subject.

17. The integrated brain-mapping system of claim 1, wherein the integrated RF-EEG cap is sized and configured to provide an MRI field-of-view (FOV) and EEG data extending over an entire brain of a subject.

18. The integrated brain-mapping system of claim 1, wherein the plurality of RF coils comprises at least 12 RF coils.

19. The integrated brain-mapping system of claim 1, wherein each of the plurality of RF coils is positioned to at least partially overlap a neighboring RF coil of the plurality of RF coils.

20. The integrated brain-mapping system of claim 1, wherein each of the plurality of RF coils comprises a flexible RF element.

21. The integrated brain-mapping system of claim 1, wherein each of the plurality of RF coils comprises a PIN diode configured to detune a respective RF coil.

22. The integrated brain-mapping system of claim 1, wherein each of the plurality of RF coils comprises a fuse configured to block RF transmit power if the PIN diode fails.

23. The integrated brain-mapping system of claim 16, further comprising an MR-compatible neuro-navigation system comprising a user interface configured to display a relative location of the TMS coil with respect to an anatomical image of the subject.

24. The integrated brain-mapping system of claim 16, further comprising one or more additional TMS coils, wherein the TMS coil and the additional TMS coils form a TMS coil array.

25. A method for causal functional brain mapping of a subject using magnetic resonance imaging (MRI), electroencephalogram (EEG), and transcranial magnetic stimulation (TMS), wherein the method comprises:

placing an integrated radiofrequency (RF)-EEG cap on a head of a subject to perform a causal functional brain mapping procedure, wherein the integrated RF-EEG cap comprises:

an EEG cap comprising a first layer of material containing a first plurality of holes that provide placeholders configured to receive EEG electrodes;

an RF cap comprising a second layer of material containing a second plurality of holes and a plurality of RF coils fixed onto the second layer of material; and one or more fasteners configured to co-register the second plurality of holes to the first plurality of holes and to removably secure the RF cap to the EEG cap;

positioning EEG electrodes through the placeholders onto a scalp of the subject; and positioning a TMS coil configured to produce a magnetic field over a head of the subject and outside the integrated RF-EEG cap;

performing the causal functional brain mapping procedure by:

acquiring MRI data by performing a pulse sequence using an MRI system and the plurality of RF coils and acquiring EEG data using the EEG electrodes;

applying TMS at a trigger time using the TMS coil; and determining localized TMS-elicited brain responses based on the MRI data and EEG data.

26. The method for causal functional brain mapping of claim 25, wherein acquiring MRI data comprises performing functional MRI (fMRI).

27. The method for causal functional brain mapping of claim 25, wherein acquiring MRI data comprises performing accelerated MRI using the plurality of RF coils.

28. The method for causal functional brain mapping of claim 25, further comprising monitoring a temperature of the EEG electrodes using one or more optical sensor probes.

29. The method for causal functional brain mapping of claim 25, wherein positioning the TMS coil further comprises determining a position of the TMS coil based on at least one of the MRI data or the EEG data.

30. The method for causal functional brain mapping of claim 25, wherein the trigger time is determined based on at least one of the MRI data or EEG data.

31. The method for causal functional brain mapping of claim 30, wherein the trigger time is determined as a predefined phase of EEG oscillations.

32. The method for causal functional brain mapping of claim 25, wherein the method further comprises determining a pause in the pulse sequence; and wherein the TMS is applied during the pause.

33. The method for causal functional brain mapping of claim 25, wherein the RF-EEG cap further comprises a plurality of cables that connect the EEG electrodes to an EEG amplifier; and
    wherein the method further comprises:
        characterizing an electric field of the plurality of RF coils; and
        routing the plurality of cables through a path of minimal electric field based on the characterized electric field.

34. The method for causal functional brain mapping of claim 25, further comprising positioning one or more additional TMS coils configured to produce a magnetic field over a head of the subject and outside the integrated RF-EEG cap;
    wherein the TMS coil and the one or more additional TMS coils form a TMS coil array; and
    wherein applying TMS at a trigger time using the TMS coil further comprises applying TMS using the TMS coil array.

* * * * *